(12) United States Patent
Tally et al.

(10) Patent No.: US 6,846,625 B1
(45) Date of Patent: Jan. 25, 2005

(54) METHOD FOR IDENTIFYING VALIDATED TARGET AND ASSAY COMBINATION FOR DRUG DEVELOPMENT

(75) Inventors: Francis P. Tally, Lincoln, MA (US); Jianshi Tao, North Andover, MA (US); Philip A. Wendler, Sudbury, MA (US); Gene Connelly, Waltham, MA (US); Paul L. Gallant, Dedham, MA (US)

(73) Assignee: Cubist Pharmaceuticals, Inc., Lexington, MA (US)

(*) Notice: Subject to any disclaimer, the term of this patent is extended or adjusted under 35 U.S.C. 154(b) by 0 days.

(21) Appl. No.: 09/227,687

(22) Filed: Jan. 8, 1999

Related U.S. Application Data

(60) Provisional application No. 60/070,965, filed on Jan. 9, 1998, provisional application No. 60/076,638, filed on Mar. 3, 1998, provisional application No. 60/081,753, filed on Apr. 14, 1998, provisional application No. 60/085,844, filed on May 18, 1998, provisional application No. 60/089,828, filed on Jun. 19, 1998, provisional application No. 60/094,698, filed on Jul. 30, 1998, provisional application No. 60/100,211, filed on Sep. 14, 1998, provisional application No. 60/101,718, filed on Sep. 24, 1998, and provisional application No. 60/107,751, filed on Nov. 10, 1998.

(51) Int. Cl.$^7$ .......................... C12Q 1/68; A01N 63/00; C12N 15/00; C12N 15/09; C07H 21/04
(52) U.S. Cl. ........................... 435/6; 435/69.1; 435/29; 435/320.1; 435/7.1; 435/253.3; 435/325; 435/455; 435/471; 536/23.1; 514/44; 424/93.1; 424/93.2; 424/93.21; 424/93.4; 424/93.42
(58) Field of Search ........................... 435/6, 7.1, 29, 435/320.1, 69.1, 252.3, 325, 455, 471; 536/23.1; 514/44; 424/93.1, 93.2, 93.21, 93.4, 93.42

(56) References Cited

U.S. PATENT DOCUMENTS

| | | | |
|---|---|---|---|
| 5,639,595 A | 6/1997 | Mirabelli et al. | 435/6 |
| 5,650,135 A * | 7/1997 | Contag et al. | 424/9.1 |
| 5,702,892 A | 12/1997 | Mulligan-Kehoe | 435/6 |
| 5,824,520 A | 10/1998 | Mulligan-Kehoe | 435/91.41 |
| 5,981,182 A * | 11/1999 | Jacobs et al. | 435/6 |
| 6,309,669 B1 * | 10/2001 | Setterstrom et al. | 424/486 |

FOREIGN PATENT DOCUMENTS

| | | |
|---|---|---|
| GB | 2303209 A | 2/1997 |
| WO | WO 91/17260 | 11/1991 |
| WO | WO 95/34575 | 12/1995 |
| WO | WO 96/04557 | 2/1996 |
| WO | WO 96/40979 | * 12/1996 |
| WO | WO 97/14812 | 4/1997 |
| WO | WO 97/27212 | 7/1997 |
| WO | WO 98/07886 | 2/1998 |
| WO | WO 98/46796 | 10/1998 |
| WO | WO 99/06839 | 2/1999 |
| WO | WO 99/36554 | 7/1999 |

OTHER PUBLICATIONS

Kernodle, et al. Infection and Immunity. vol. 65, No. 1, pp. 179–184, Jan. 1997.*
Kernodle, D.S., et al., "Expression of an Antisense *hla* Fragment in *Staphylococcus aureus* Reduces Alpha–Toxin Production In Vitro and Attenuates Lethal Activity in a Murine Model," *Infect. Immun.*, 65:179–184 (1997).
Pines, O., et al., "Expression of Double–Stranded–RNA Specific RNase III of *Escherichia coli* Is Lethal to *Saccharomyces cerevisiae*," *J. Bacteriol.*, 170:2989–2993 (1998).
Ball, K.L., et al., "Cell–cycle Arrest and Inhibition of Cdk4 Activity by Small Peptides Based on the Carboxy–terminal Domain of p21$^{WAF1}$," *Current Biology*, 7:71–80 (1996).
Sparks, A.B., et al., "Identification and Characterization of Src SH3 Ligands from Phage–displayed Random Peptide Libraries," *J. Biol. Chem.*, 269:23853–23856 (1994).
Colas, P., et al., "Genetic Selection of Peptide Aptamers that Recognize and Inhibit Cyclin–dependent Kinase 2," *Nature*, 380:548–550 (1996).
Kay, B.K., et al., "From Peptides to Drugs via Phage Display," *DDT*, 3:370–378 (1998).
Mao, J–R., et al., "Gene Regulation by Antisense DNA Produced in Vivo," *J. Biol. Chem.*, 270(34) :19684–19687 (1995).
Holzmayer, T.A., et al., "Isolation of dominant negative mutants and inhibitory antisense RNA sequences by expression selection of random DNA fragments," *Nucleic Acids Res.*, 20 (4) :711–717 (1992).

* cited by examiner

*Primary Examiner*—Gerry Leffers

(57) ABSTRACT

The invention comprises methods useful within a larger process for identifying compounds and/or designing further compounds with activity to produce a desired phenotype (for example, growth inhibition) in cells whose target cell component is the subject of certain studies to identify such compounds. The invention employs constructed cells comprising a regulable gene encoding a biomolecule which modulates (inhibits or activates) in vivo the function of a target component of the cell which can be an enzyme for example. The process incorporates methods for identifying biomolecules that bind to a chosen target cell component in vitro, methods for identifying biomolecules that also bind to the chosen target and modulate its function intracellularly, causing a phenotypic effect. The intracellular effect of a biomolecule can be tested in cell culture, or tested after introduction of the constructed cells into a host mammal in vivo, and methods for identifying compounds that compete with the biomolecules for sites on the target in competitive binding assays. Compounds identified by the series of steps in this process are candidates for drugs with the desired activity on the cell. Targets for which such compounds can be identified are validated as being essential to a phenotype of the cell.

43 Claims, 8 Drawing Sheets

METHOD FOR IDENTIFYING VALIDATED TARGET AND ASSAY COMBINATION FOR DRUG DEVELOPMENT

RELATED APPLICATIONS

This application claims the benefit of U.S. Patent Application Number 60/070,965 filed on Jan. 9, 1998; U.S. Patent Application No. 60/076,638 filed on Mar. 3, 1998; U.S. Patent Application No. 60/081,753 filed on Apr. 14, 1998; U.S. Patent Application Number 60/085,844 filed on May 18, 1998; U.S. Patent Application No. 60/089,828 filed on Jun. 19, 1998; U.S. Patent Application Number 60/094,698 filed on Jul. 30, 1998; U.S. Patent Application Number 60/100,211 filed on Sep. 14, 1998; U.S. Patent Application No. 60/101,718 filed on Sep. 24, 1998; and U.S. Patent Application No. 60/107,751 filed on Nov. 10, 1998. The teachings of each of these referenced applications are incorporated herein by reference in their entirety.

BACKGROUND OF THE INVENTION

In the discovery and development of new drugs, it is a common strategy to first try to identify molecules or complexes of molecules, naturally occurring within cells, that are involved in producing symptoms of a disease. These naturally occurring molecules can be thought of as "targets." A second major part of the strategy is then to find molecules that bind to the targets. These molecules are candidates for drug development, on the theory that a molecule that binds to a target can modulate (inhibit or enhance) the function of the target, thereby causing a change in the biological status of the cell containing the target. The change caused in the cell (e.g., a change in phenotype towards wildtype, or a change in growth rate) may be therapeutically beneficial to the animal or human host of the cell.

The genomics revolution, by determining the DNA sequences of great numbers of genes from many different organisms, has considerably broadened the possibilities for drug discovery by identifying large numbers of molecules that are potential targets of drug action. These technical advances in genomics however, have posed an entirely new set of challenges. Specifically, how can one prove that a chosen target molecule is essential to maintaining the disease or disorder to be treated? That is, how does one validate a target? (See "target validation" in Definitions.)

Although methods currently available to validate targets do provide some guidelines in selection of drug targets, they are usually not conducted under the conditions in which a drug actually interacts with its target, and therefore provide a limited set of information. In addition, they do not directly address, among other things: 1) if a wild type (normal) target is essential for cell growth and viability during the disease state; 2) if the wild type gene products themselves are suitable targets for drug discovery; 3) if specific sites on a target are suitable for drug interaction (for example, in a pathogenic organism, there can be one gene coding for a single protein target with two activities—one activity essential for growth and infectivity, the second activity nonessential); 4) if a compensatory mechanism in the cell, either in vitro or in vivo, can overcome or compensate for target modulation or, 5) if a disease state can be cured by modulation of function of the candidate target. These methods also do not provide a direct route for testing wild type target proteins in high throughput screening assays.

An analysis of the discovery of novel antimicrobial agents illustrates the problems researchers in all fields of drug development face today. The increasing prevalence of drug-resistant pathogens (bacteria, fungi, parasites, etc.) has led to significantly higher mortality rates from infectious diseases and currently presents a serious crisis worldwide. Despite the introduction of second and third generation antimicrobial drugs, certain pathogens, such as vancomycin resistant strains of *Enterococcus facieum*, have developed resistance to all currently available drugs. New antimicrobial drugs must be discovered to treat such infections by such organisms, and new methods are urgently needed to facilitate making such discoveries.

Neither whole cell screening, chemistry nor target based drug discovery approaches as currently applied, have met the challenge of controlling infectious diseases, particularly those caused by drug resistant microorganisms. Whole cell screening assays have been limited by the fact that they are unable to identify compounds that can effectively modulate a target function inside the cell but cannot permeate the cell membrane to get to the target. Therefore entire classes of potent, intracellular target modulators, which could be subsequently modified by medicinal chemistry to increase cell membrane permeability, go undetected. Chemistry based approaches have focused on chemically modifying the molecular structure of existing antimicrobial drugs or combining existing antimicrobials with another agent to circumvent established resistance mechanisms. Technical advances in molecular biology, automated methods for high throughput screening and chemical syntheses have led to an increase in the number of target based screens utilized for antimicrobial drug discovery and in the number of compounds being analyzed. However, despite these advances, only a limited number of antimicrobial drugs acting by a novel mechanism have been identified during recent years.

How does one efficiently establish screening assays for drugs that can be used with a variety of different targets having different properties, enzymatic activities, or even unknown functions? A number of potentially novel, valuable targets are incompatible with current methods to screen for drug candidates because either the target's exact function and molecular mechanism of action are unknown, or there are technical obstacles preventing the development of effective high throughput screening methods. It can take anywhere from six months to several years to develop a screening assay, which is impractical when the goal is to rapidly screen multiple targets in a cost-effective manner.

The path in the progression from target identification through assay development, high throughput screening, medicinal chemistry, lead optimization, preclinical and clinical drug development is expensive, time consuming and full of technical challenges. Many different targets must be screened against multiple chemical compounds to identify new lead compounds for drug development. New, efficient technologies are needed that can be broadly applied to a variety of different targets to validate targets in the direct context of the desired outcome of drug therapy and to rapidly develop screening assays using these targets for drug discovery. Such developments will allow the wealth of genomics information to be leveraged for drug discovery and will lower the risk and costs while expediting the timelines of the drug discovery process.

SUMMARY OF THE INVENTION

The invention relates to methods that couple the validation of a target (see Definitions) for drug discovery with the development of an assay to identify compounds that cause a phenotypic effect on the target cell. These procedures can be applied to identifying compounds that bind to and modulate the function of target components of a cell whose function is known or unknown, and cell components that are not amenable to other screening methods.

The invention relates to procedures for identifying a compound that binds to and modulates (inhibits or enhances) the function of a component of a cell, thereby producing a phenotypic effect in the cell. Within these procedures are methods for identifying a biomolecule (See Definitions section) that 1) binds to, in vitro, a component of a cell that has been isolated from other constituents of the cell and that 2) causes, in vivo, as seen in an assay upon intracellular expression of the biomolecule, a phenotypic effect (See Definitions section) in the cell which is the usual producer and host of the target cell component. In an assay demonstrating characteristic 2) above, intracellular production of the biomolecule can be in cells grown in culture or in cells introduced into an animal. Further methods within these procedures are those methods comprising an assay for a phenotypic effect in the cell upon intracellular production of the biomolecule, either in cells in culture or in cells that have been introduced into one or more animals, and an assay to identify one or more compounds that behave as competitors of the biomolecule in an assay of binding to the target cell component.

One procedure envisioned in the invention is a process for identifying one or more compounds that produce a phenotypic effect on a cell. The process is at the same time a method for target validation (See Definitions section). The process is characterized by identifying a biomolecule which binds an isolated target cell component, constructing cells comprising the target cell component and further comprising a gene encoding the biomolecular binder which can be expressed to produce the biomolecular binder, testing the constructed cells for their ability to produce, upon expression of the gene encoding the biomolecular binder, a phenotypic effect in the cells (e.g., inhibition of growth), wherein the test of the constructed cells can be a test of the cells in culture or a test of the cells after introducing them into host animals, or both, and further, identifying, for a biomolecular binder that caused the phenotypic effect, one or more compounds that compete with the biomolecular binder for binding to the target cell component.

A test of the constructed cells after introducing them into host animals is especially well-suited to assessing whether a biomolecular binder can produce a particular phenotype by the expression (regulatable by the researcher) of a gene encoding the biomolecular binder. In this method, cells are constructed which have a gene encoding the biomolecular binder, and wherein the biomolecular binder can be produced by regulation of expression of the gene. The constructed cells are introduced into a set of animals. Expression of the gene encoding the biomolecular binder is regulated in one group of the animals (test animals) such that the biomolecular binder is produced. In another group of animals, the gene encoding the biomolecular binder is regulated such that the biomolecular binder is not produced (control animals). The cells in the two groups of animals are monitored for a phenotypic change (for example, a change in growth rate). If the phenotypic change is observed in cells in the test animals and not in the cells in the control animals, or to a lesser extent in the control animals, then the biomolecular binder has been proven to be effective in binding to its target cell component under in vivo conditions.

A further embodiment of the invention is a method for determining whether a target cell component of a particular cell type (a "first cell") is essential to producing a phenotypic effect on the first cell, the method having the steps: isolating the target component of the first cell; identifying a biomolecular binder of the isolated target component of the first cell; constructing a second type of cells ("second cell") comprising the target component and a regulable, exogenous gene encoding the biomolecular binder; and testing the second cell in culture for an altered phenotypic effect, upon production of the biomolecular binder in the second cell; whereby, if the second cell shows the altered phenotypic effect upon production of the biomolecular binder, then the target component of the first cell is essential to producing the phenotypic effect on the first cell. The target cell component in this embodiment and in other embodiments not limited to pathogens can be one that is found in mammalian cells, especially cells of a type found to cause or contribute to disease or the symptoms of disease (e.g., cells of tumors or cells of other types of hyperproliferative disorders).

The invention further relates to methods particularly well suited to a procedure for identifying and/or designing compounds with antimicrobial activity against a pathogen whose target cell component is the subject of studies to identify such compounds. A common mechanism of action of an antimicrobial agent is binding to a component of the cells of the pathogen treated with the antimicrobial. The procedure includes methods for identifying biomolecules that bind to a chosen target in vitro, methods for identifying biomolecules that also bind to the chosen target and modulate its function during infection of a host mammal in vivo, and methods for identifying compounds that compete with the biomolecules for sites on the target in competitive binding assays. Compounds identified by this procedure are candidates for drugs with antimicrobial activity against the pathogen.

One embodiment of the invention is a method for identifying a biomolecular inhibitor of growth of pathogen cells by using cell culture techniques, comprising contacting one or more types of biomolecules with isolated target cell component of the pathogen, applying a means of detecting bound complexes of biomolecules and target cell component, whereby, if the bound complexes are detected, one or more types of biomolecules have been identified as a biomolecular binder of the target cell component, constructing a pathogen strain having a regulable gene encoding the biomolecular binder, regulating expression of the gene encoding the biomolecular binder to express the gene; and monitoring growth of the pathogen cells in culture relative to suitable control cells, whereby, if growth of the pathogen cells is decreased compared to growth of suitable control cells, then the biomolecule is a biomolecular inhibitor of growth of the pathogen cells.

A further embodiment of the invention is a method, employing an animal test, for identifying one or more compounds that inhibit infection of a mammal by a pathogen by binding to a target cell component, comprising constructing a pathogen comprising a regulable gene encoding a biomolecule which binds to the target cell component, infecting test animals with the pathogen, regulating expression of the regulable gene to produce the biomolecule, monitoring the test animals and suitable control animals for signs of infection, wherein observing fewer or less severe signs of infection in the test animals than in suitable control animals indicates that the biomolecule is a biomolecular inhibitor of infection, and identifying one or more compounds that compete with the biomolecular inhibitor of growth for binding to the target cell component (as by employing a competitive binding assay), then the compound inhibits infection of a mammal by a pathogen by binding to a target.

The competitive binding assay to identify binding analogs of biomolecular binders, which have been proven to bind to their targets in an intracellular test of binding, can be applied to any target for which a biomolecular binder has been identified, including targets whose function is unknown or targets for which other types of assays are not easily developed and performed. Therefore, the method of the invention offers the advantage of decreasing assay development time when using a gene product of known function as a target cell component and the advantage of bypassing the major hurdle of gene function identification when using a gene product of unknown function as a target cell component.

Other embodiments of the invention are cells comprising a biomolecule and a target cell component, wherein the biomolecule is produced by expression of a regulable gene, and wherein the biomolecule modulates function of the target cell component, thereby causing a phenotypic change in the cells. Yet other embodiments are cells comprising a biomolecule and a target cell component, wherein the biomolecule is a biomolecular binder of the target cell component, and is encoded by a regulable gene. The cells can include mammalian cells or cells of a pathogen, for instance, and the phenotypic change can be a change in growth rate. The pathogen can be a species of bacteria, yeast, fungus, or parasite, for example.

DETAILED DESCRIPTION OF THE INVENTION

Definitions

Figure 1:
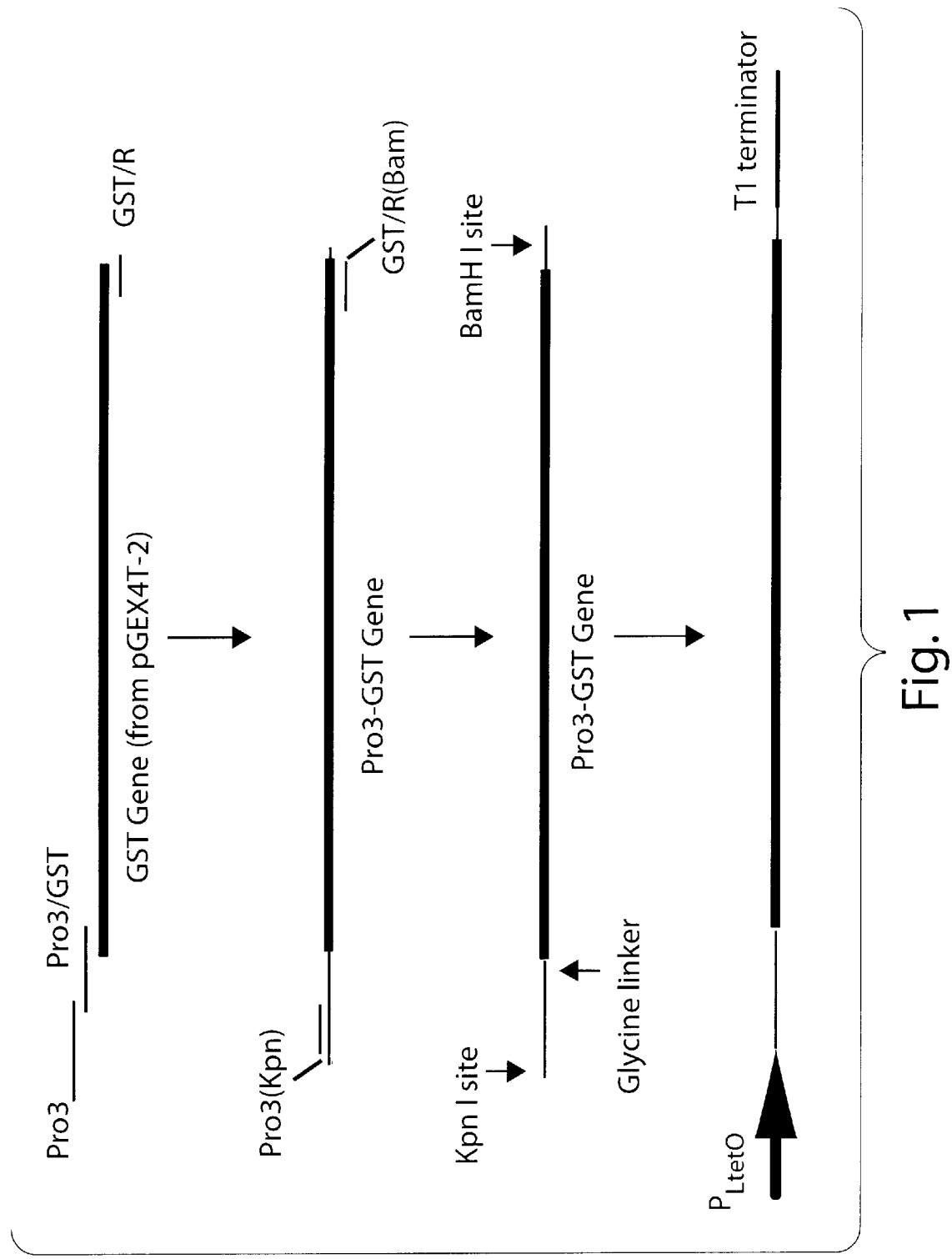
FIG. 1 is an illustration showing the steps in cloning of the Pro-3 peptide for regulated expression as a GST (glutathione-S transferase) fusion protein. See Example 1.

Target: (also, "target component of a cell," or "target cell component") a constituent of a cell which contributes to and is necessary for the production or maintenance of a phenotype of the cell in which it is found. A target can be a single type of molecule or can be a complex of molecules. A target can be the product of a single gene, but can also be a complex comprising more than one gene product (for example, an enzyme comprising a and P subunits, mRNA, tRNA, ribosomal RNA or a ribonucleoprotein particle such as a snRNP). Targets can be the product of a characterized gene (gene of known function) or the product of an uncharacterized gene (gene of unknown function).

Target Validation: the process of determining whether a target is essential to the maintenance of a phenotype of the cell type in which the target normally occurs. For example, for pathogenic bacteria, researchers developing antimicrobials want to know if a compound which is potentially an antimicrobial agent not only binds to a target in vitro, but also binds to, and modulates the function of, a target in the bacteria in vivo, and especially under the conditions in which the bacteria are producing an infection—those conditions under which the antimicrobial agent must work to inhibit bacterial growth in an infected animal or human. If such compounds can be found that bind to a target in vitro and alter the targets function in cells resulting in an altered phenotype, as found by testing cells in culture and/or as found by testing cells in an animal, then the target is validated.

Phenotypic Effect: a change in an observable characteristic of a cell which can include, e.g., growth rate, level or activity of an enzyme produced by the cell, sensitivity to various agents, antigenic characteristics, and level of various metabolites of the cell. A phenotypic effect can be a change away from wild type (normal) phenotype, or can be a change towards wild type phenotype, for example. A phenotypic effect can be the causing or curing of a disease state, especially where mammalian cells are referred to herein. For cells of a pathogen or tumor cells, especially, a phenotypic effect can be the slowing of growth rate or cessation of growth.

Biomolecule: a molecule which can be produced as a gene product in cells that have been appropriately constructed to comprise one or more genes encoding the biomolecule. Preferably, production of the biomolecule can be turned on, when desired, by an inducible promoter. A biomolecule can be a peptide, polypeptide, or an RNA or RNA oligonucleotide, a DNA or DNA oligonucleotide, but is preferably a peptide. The same biomolecules can also be made synthetically. For peptides, see Merrifield, J., *J. Am. Chem. Soc.* 85: 2140–2154 (1963). For instance, an Applied Biosystems 431A Peptide Synthesizer (Perkin Elmer) can be used for peptide synthesis. Biomolecules produced as gene products intracellularly are tested for their interaction with a target in the intracellular steps described herein (tests performed with cells in culture and tests performed with cells that have been introduced into animals). The same biomolecules produced synthetically are tested for their binding to an isolated target in an initial in vitro method described herein. Synthetically produced biomolecules can also be used for a final step of the method for finding compounds that are competitive binders of the target.

Biomolecular Binder (of a target): a biomolecule which has been tested for its ability to bind to an isolated target cell component in vitro and has been found to bind to the target.

Biomolecular Inhibitor of Growth: a biomolecule which has been tested for its ability to inhibit the growth of cells constructed to produce the biomolecule in an "in culture" test of the effect of the biomolecule on growth of the cells, and has been found, in fact, to inhibit the growth of the cells in this test in culture.

Biomolecular Inhibitor of Infection: a biomolecule which has been tested for its ability to ameliorate the effects of infection, and has been found to do so. In the test, pathogen cells constructed to regulably express the biomolecule are introduced into one or more animals, the gene encoding the biomolecule is regulated so as to allow production of the biomolecule in the cells, and the effects of production of the biomolecule are observed in the infected animals compared to one or more suitable control animals.

Isolated: term used herein to indicate that the material in question exists in a physical milieu distinct from that in which it occurs in nature. For example, an isolated target cell component of the invention may be substantially isolated with respect to the complex cellular milieu in which it naturally occurs. The absolute level of purity is not critical, and those skilled in the art can readily determine appropriate levels of purity according to the use to which the material is to be put. In many circumstances the isolated material will form part of a composition (for example, a more or less crude extract containing other substances), buffer system or reagent mix. In other circumstances, the material may be purified to essential homogeneity, for example as determined by PAGE or column chromatography (for example, HPLC).

Pathogen or Pathgenic Organism: an organism which is capable of causing disease, detectable by signs of infection or symptoms characteristic of disease. Pathogens can include procaryotes (which include, for example, medically significant Gram-positive bacteria such as *Streptococcus pneumoniae, Enterococcus faecalis* and *Staphylococcus aureus*, Gram-negative bacteria such as *Escherichia coli, Pseudomonas aeroginosa* and *Klebsiella pneumoniae*, and "acid-fast" bacteria such as Mycobacteria, especially *M. tuberculosis*), eucaryotes such as yeast and fingi (for example, *Candida albicans* and *Aspergillus fumigatus*) and parasites. It should be recognized that pathogens can include such organisms as soil-dwelling organisms and "normal flora" of the skin, gut and orifices, if such organisms colonize and cause symptoms of infection in a human or other mammal, by abnormal proliferation or by growth at a site from which the organism cannot usually be cultured.

The present invention relates to methods that couple the validation of a target cell component for drug discovery with the development of a validated assay to identify compounds that cause a phenotypic effect on the target cell (cell harboring the target cell component). When the target cells are cells of a pathogenic organism, compounds identified by this procedure are candidates for drugs with antimicrobial activity against the pathogen.

The method utilized for target validation provides a test of how a biomolecule produced intracellularly binds to a specific site on a target cell component and alters the target's function in a cell during an established infection or disease. The technology to validate the target identifies a biomolecule specific to the target that can be used in a screening assay to identify drug leads, thereby coupling target validation with drug lead identification. The method also validates specific sites on a target molecule for drug discovery, which is especially important for proteins involved in multiple functions.

Described herein are methods that result in the identification of compounds that cause a phenotypic effect on a cell. The general steps described herein to find a compound for drug development can be thought of as these: (1) identifying a biomolecule that can bind to an isolated target cell component in vitro, (2) confirming that the biomolecule, when produced in cells with the target cell component, can cause a desired phenotypic effect and (3) identifying, by an in vitro screening method, for example, compounds that compete with the biomolecule for binding to the target cell component. Advantages of the these steps are that it is not necessary to identify the function of the target cell component and it is not necessary to develop an assay tailored to the function (e.g., enzyme activity) of the target cell component.

Central to these methods is general step (2) above, intracellular validation of a biomolecule comprising one or more steps that determine whether a biomolecule can cause a phenotypic effect on a cell, when the biomolecule is produced by the expression (which can be regulable) of a gene in the cell. As used in general step (2), a biomolecule is a gene product (e.g., polypeptide, RNA, peptide or RNA oligonucleotide) of an exogenous gene—a gene which has been introduced in the course of construction of the cell. See also Definitions section.

Biomolecules that bind to and alter the function of a candidate target are identified by various in vitro methods. Upon production of the biomolecule within a cell either in vitro or within an animal model system, the biomolecule binds to a specific site on the target, alters its intracellular function, and hence produces a phenotypic change (e.g. cessation of growth, cell death). When the biomolecule is produced in engineered pathogen cells in an animal model of infection, cessation of growth or death of the engineered pathogen cells leads to the clearing of infection and animal survival, demonstrating the importance of the target in infection and thereby validating the target.

A method for (1) identifying a biomolecule that produces a phenotypic effect on a cell (wherein the cell can be, for instance, a pathogen cell or a mammalian cell) and (2) simultaneous intracellular target validation, can comprise steps of introducing into an animal a cell comprising an exogenous regulable gene encoding the biomolecule, regulating expression of the gene to produce the biomolecule in the cell, and monitoring said cell in the animal for a phenotypic effect, compared to a suitable control cell. If the cell of this test manifests a phenotypic effect, this indicates that the biomolecule produced in the cell causes a phenotypic effect on the cell. If this phenotypic effect is the inhibition of growth of the cells, then the biomolecule can be termed a "biomolecular inhibitor" or a "biomolecular inhibitor of growth." It may be desirable to perform another test of intracellular function, using cell culturing techniques, wherein the cell comprising an exogenous regulable gene encoding the biomolecule of interest, and comprising the target cell component, is treated so as to turn on expression of the gene encoding the biomolecule, and one or more phenotypic characteristics of the cells in culture are monitored relative to suitable control cells, where the control cells do not produce the biomolecule. It may be preferable, where both "in culture" and "in animal" intracellular tests are performed, to do an "in culture" test first.

The purpose of intracellular validation for the combination of a potential target for drug action and molecule for drug development is two-fold. First, it demonstrates that the biomolecule under study produces a phenotypic effect on a living cell. In contrast with conditions in an in vitro binding test, the biomolecule in an intracellular test is exposed to a multitude of potential binding partners in the living cell, and interaction with one or more of these binding partners in the cell may be unproductive or result in undesirable effects. These effects are not detectable in an in vitro binding test. Second, where a biomolecule has been shown previously by in vitro tests to bind to a target cell component (that is, the biomolecule can be called a "biomolecular binder" of the target cell component; See Definitions section), intracellular validation provides proof that the target cell component is essential to the maintenance of the original phenotype of the cell. Therefore, the target is validated for drug discovery and the biomolecule can then be utilized in a competitive binding assay to identify compounds that will have an effect on target molecule function.

Efficient binding between a biomolecule and a target cell component may be demonstrated in vitro; even binding that inhibits activity of a target enzyme may be demonstrated in vitro. However, in the living cells, there could exist a redundant system that nullifies the effect of the biomolecule binding to the target cell component. For example, production of an enzyme having similar activity to that of the target cell component may be induced in the cells. By a mechanism such as this, the cell could escape any effect the biomolecule might otherwise cause by binding to the target cell component.

Using an intracellular test to validate biomolecule/target cell component interaction is superior to using only an in vitro test using isolated molecules, because the intracellular test ensures that the target cell component is in its natural conformation and that the biomolecule "sees" the target cell component in that conformation, as that conformation occurs in a disease state. That in an intracellular test a biomolecule finds a site which ultimately causes a phenotypic effect on the cell indicates that the biomolecule is binding to a functionally relevant site on the target cell component (e.g., an active site of an enzyme). Thus, molecules that are found to be structural analogs of the biomolecule and to compete with the biomolecule for a binding site on the target will also interact with the functionally relevant site of the target cell component, as functional analogs. A functional analog of the biomolecule can be found through competitive binding assays of the biomolecule against compounds (as in a library of compounds) that are potential binders of the target cell component. Structural analogs can also be found by rational drug design once a biomolecular binder is identified, by designing drugs that mimic the structure of the biomolecular binder. These structural analogs can be tested for their binding properties by techniques described herein.

A further advantage of the intracellular test in which the biomolecule is produced from one or more genes in the cell, is that the biomolecule does not have to pass through a cell membrane or rely on inefficient uptake mechanisms of the cell. Intracellular production of the biomolecule ensures that a biomolecule that interacts with a functional site on a target cell component to produce an effect will be detected, even if uptake of the biomolecule into the cell is limited. By the intracellular test, more biomolecules testing as being able to cause the desired phenotypic effect can be detected as candidates for further testing to find functional analogs for drug development. In a test employing extracellular addition of biomolecules, biomolecules that bind the target cell component but are taken up by the cell only to a limited extent could be missed as candidates for further testing to find functional analogs for drug development. Limited uptake of a biomolecule which has been found to bind to a target in vitro is not necessarily a barrier to further steps towards drug development, as a structural portion of the ultimate compound to be administered as a drug can be selected for its stability, membrane solubility, efficient uptake, etc., and can be chemically combined with a compound whose structure mimics the active binding portion of the biomolecule. Intracellular production of the biomolecule, in an intracellular test of the effect of a biomolecule, as opposed to uptake from outside the cell, can also minimize degradation of the biomolecules from extracellular and intracellular degradative enzymes (e.g., proteases).

In further steps following one or more intracellular tests of the biomolecule/target cell component combination, one or more compounds that can also produce the phenotypic effect caused by the biomolecule can be identified in an in vitro competitive binding assay (which may be adapted for high-throughput screening) as compounds that compete with the biomolecule for a binding site on the target cell component. Target cell components can be isolated from the type of cell in which the phenotypic effect is desired (for instance, cells of pathogenic bacteria, yeast or fungi; mammalian cells, such as tumor cells), or from cells engineered to produce the cell component or a derivative of the cell component that would provide (at least some) structurally identical binding sites (e.g., a fusion protein). Compounds that produce the phenotypic effect observed with the biomolecule can be found in the competitive binding assay upon screening of libraries of compounds (for example, small molecule compounds or natural products or libraries that can be selected for having as their members compounds that have greater intracellular stability than biomolecules such as peptides or RNA oligonucleotides).

The invention includes methods for identifying compounds that inhibit the growth of cells having a target cell component. The target cell component can first be identified as essential to the growth of the cells in culture and/or under conditions in which it is desired that the growth of the cells be inhibited. These methods can be applied, for example, to various types of cells that undergo abnormal or undesirable proliferation, including cells of neoplasms (tumors or growths, either benign or malignant) which, as known in the art, can originate from a variety of different cell types. Such cells can be referred to, for example, as being from adenomas, carcinomas, lymphomas or leukemias. The method can also be applied to cells that proliferate abnormally in certain other diseases, such as arthritis, psoriasis or autoimmune diseases.

Described herein are similar methods for identifying inhibitors of target molecules or target cell components of pathogenic organisms. These methods can include a target validation procedure using an animal model for confirming that a cell component of a pathogenic organism is essential, after infection with the organism has been established in a host, and that the inhibitor is effective against the organism after the organism has established the infection. A goal of the procedure is to identify compounds and/or gain the knowledge required to design compounds that can be used as antimicrobial agents to treat a human or other mammal having an infection of the organism.

The invention provides methods for in vitro and in vivo validation of target and assay combinations. Following selection of biomolecular binders to the isolated target cell component of interest, the invention can incorporate steps for (1) regulable (e.g., inducible) intracellular expression of a gene encoding the biomolecular binder and (2) monitoring cell viability in culture (e.g., cell growth in liquid media or agar plates) or in vivo (e.g., growth of introduced cells or pathogen virulence in an animal infection model) or both. If intracellular expression of the biomolecular binder inhibits the function of a target essential for growth (presumably by binding to the target at a biologically relevant site) cells monitored in step (2) will exhibit a slow growth or no growth phenotype. Targets found to be essential for growth by these methods are validated starting points for drug discovery, and can be incorporated into assays to identify more stable compounds that bind to the same site on the target as the biomolecule.

Where the cells are pathogen cells and the desired phenotypic change to be monitored is inhibition of growth, the invention provides a procedure to examine the activity of target (pathogen) cell components in an animal infection model. Controlled expression in cells of biomolecular binders to the target of interest mimics the environment for traditional antimicrobial therapy and validates targets as essential and appropriate for drug discovery. The technology facilitates choosing the best antimicrobial targets for drug discovery by facilitating direct observation of the effect (phenotype) produced by target inhibition at a specific target subsite. The process is broadly applicable to a variety of targets. The process also validates target and biomolecular binder combinations as a direct path to high throughput screening for binding analogs of the biomolecular binder, and is equally facile with targets that are gene products of genes of unknown function or genes of known function. Validated target and biomolecular binder assay combinations can be used directly in in vitro or in vivo competitive binding assays for screening chemical compound files. Compounds that compete with the biomolecular binders are identified as potential medicinal chemistry leads.

In the course of this method, it may be decided to study as a target cell component a gene product of a particular cell type (e.g., a type of pathogenic bacteria), wherein the target cell component is already known as being encoded by a characterized gene, as a potential target for a modulator to be identified. In this case, the target cell component can be isolated directly from the cell type of interest, assuming suitable culture methods are available to grow a sufficient number of cells, using methods appropriate to the type of cell component to be isolated (e.g., protein purification methods such as differential precipitation, ion exchange chromatography, gel chromatography, affinity chromatography, HPLC). Alternatively, the target cell component can be produced recombinantly, which requires that the gene encoding the target cell component be isolated from the cell type of interest. This can be done by any number of methods, for example known methods such as PCR, using template DNA isolated from the pathogen or a DNA library produced from the pathogen DNA, and using primers based on known sequences or combinations of known and unknown sequences within or external to the chosen gene. See, for example, methods described in "The Polymerase Chain Reaction," Chapter 15 of *Current Protocols in Molecular Biology*, (Ausubel, F. M. et al., eds), John Wiley & Sons, New York, 1998. Other methods include cloning a gene from a DNA library (e.g., a cDNA library from a eucaryotic pathogen) into a vector (e.g., plasmid, phage, phagemid, virus, etc.) and applying a means of selection or screening to clones resulting from a transformation of vectors (including a population of vectors now having inserted genes) into appropriate host cells. The screening method can take advantage of properties given to the host cells by the expression of the inserted chosen gene (e.g., detection of the gene product by antibodies directed against it, detection of an enzymatic activity of the gene product), or can detect the presence of the gene itself (for instance, by methods employing nucleic acid hybridization). For methods of cloning genes in *E. coli*, which also may be applicable to cloning in other bacterial species, see, for example, "*Escherichia coli*, Plasmids and Bacteriophages," Chapter 1 of *Current Protocols in Molecular Biology*, (Ausubel, F. M. et al., eds), John Wiley & Sons, New York, 1998. For methods applicable to cloning genes of eukaryotic origin, see Chapter 5 ("Construction of Recombinant DNA Libraries"), Chapter 9 ("Introduction of DNA Into Mammalian Cells") and Chapter 6 ("Screening of Recombinant DNA Libraries") of *Current Protocols in Molecular Biology*, (Ausubel, F. M. et al., eds), John Wiley & Sons, New York, 1998.

Target proteins can be expressed with *E. coli* or other prokaryotic gene expression systems, or in eukaryotic gene expression systems. Since many eukaryotic proteins carry unique modifications that are required for their activities, e.g. glycosylation and methylation, protein expression can in some cases be better carried out in eukaryotic systems, such as yeast, insect, or mammalian cells that can perform these modifications. Examples of these expression systems have been reviewed in the following literature: Methods in Enzymology, Volume 185, eds D. V. Goeddel, Academic Press, San Diego, 1990; Geisse et al, *Protein Expression and Purification* 8:271–282, 1996; Simonsen and McGrogan, *Biologicals* 22: 85–94; Jones and Morikawa, *Current Opinions in Biotechnologies* 7: 512–516, 1996; Possee, *Current Opinions in Biotechnologies* 8:569–572.

Where a gene encoding a chosen target cell component has not been isolated previously, but is thought to exist because homologs of the gene product are known in other species, the gene can be identified and cloned by a method such as that used in Shiba et al., U.S. Pat. No. 5,759,833, Shiba et al., U.S. Pat. No. 5,629,188, Martinis et al., U.S. Pat. No. 5,656,470 and Sassanfar et al., U.S. Pat. No. 5,756,327. The teachings of these four patents are incorporated herein by reference in their entirety.

It is an advantage of the target validation method that it can be used with target cell components which have not been previously isolated or characterized and whose functions are unknown. In this case, a segment of DNA containing an open reading frame (ORF; a cDNA can also be used, as appropriate to a eukaryotic cell) which has been isolated from a cell of a type that is to be an object of drug action (e.g., tumor cell, pathogen cell) can be cloned into a vector, and the target gene product of the ORF can be produced in host cells harboring the vector. The gene product can be purified and further studied in a manner similar to that of a gene product that has been previously isolated and characterized.

In some cases, the open reading frame (in some cases, cDNA) can be isolated from a source of DNA of the cells of interest (genomic DNA or a library, as appropriate), and inserted into a fusion protein or fusion polypeptide construct. This construct can be a vector comprising a nucleic acid sequence which provides a control region (e.g., promoter, ribosome binding site) and a region which encodes a peptide or polypeptide portion of the fusion polypeptide wherein the polypeptide encoded by the fusion vector endows the fusion polypeptide with one or more properties that allow for the purification of the fusion polypeptide. For example, the vector can be one from the pGEX series of plasmids (Pharmacia) designed to produce fusions with glutathione S-transferase.

The isolated DNA having an open reading frame, whether encoding a known or an as yet unidentified gene product, when inserted into an expression construct, can be expressed to produce the target cell component in host cells. Host cells can be, for example, Gram-negative or Gram-positive bacterial cells such as *Escherichia coli* or *Bacillus subtilis*, respectively, or yeast cells such as *Saccharomyces cerevisiae, Schizosaccharomyces pombe* or *Pichia pastoris*. It is preferable that the target cell component to be used in target validation studies be produced in a host that is genetically related to the pathogen from which the gene encoding it was isolated. For example, for a Gram-negative bacterial pathogen, an *E. coli* host is preferred over a *Pichia pastoris* host. The target cell component so produced can then be isolated from the host cells. Many protein purification methods are known that separate proteins on the basis of, for instance, size, charge, or affinity for a binding partner (e.g., for an enzyme, a binding partner can be a substrate or substrate analog), and these methods can be combined in a sequence of steps by persons of skill in the art to produce an effective purification scheme. For methods to manipulate RNA, see, for example, Chapter 4 in *Current Protocols in Molecular Biology* (Ausubel, F. M. et al., eds), John Wiley & Sons, New York, 1998.

An isolated cell component or a fusion protein comprising the cell component can be used in a test to identify one or more biomolecular binders of the isolated product (general step (1)). A biomolecular binder of a target cell component (See Definitions section) can be identified by in vitro assays that test for the formation of complexes of target and biomolecular binder noncovalently bound to each other. For example, the isolated target can be contacted with one or more types of biomolecules under conditions conducive to binding, the unbound biomolecules can be removed from the targets, and a means of detecting bound complexes of biomolecules and targets can be applied. The detection of the bound complexes can be facilitated by having either the potential biomolecular binders or the target labeled or tagged with an adduct that allows detection or separation (e.g., radioactive isotope or fluorescent label; streptavidin, avidin or biotin affinity label). Alternatively, both the potential biomolecular binders and the target can be differentially labeled. For examples of such methods see, e.g., WO 98/19162.

The biomolecules to be tested for binding to a target can be from a library of candidate biomolecular binders, (e.g., a peptide or oligonucleotide library). For example, a peptide library can be displayed on the coat protein of a phage (see, for examples of the use of genetic packages such as phage display libraries, Koivunen, E. et al., *J. Biol. Chem.* 268:20205–20210 (1993)). The biomolecules can be detected by means of a chemical tag or label attached to or integrated into the biomolecules before they are screened for binding properties. For example, the label can be a radioisotope, a biotin tag, or a fluorescent label. Those molecules that are found to bind to the target molecule can be called biomolecular binders.

An isolated target cell component, an antigenically similar portion thereof, or a suitable fusion protein comprising all of or a portion of or the entire target can be used in a method to select and identify biomolecules which bind specifically to the target. Where the target cell component comprises a protein, fusion proteins comprising all of, or a portion of, the target linked to a second moiety not occurring in the target as found in nature, can be prepared for use in another embodiment of the method. Suitable fusion proteins for this purpose include those in which the second moiety comprises an affinity ligand (e.g., an enzyme, antigen, epitope). The fusion proteins can be produced by the insertion of a gene encoding a target or a suitable portion of such gene into a suitable expression vector, which encodes an affinity ligand (e.g., pGEX-4T-2 and pET-15b, encoding glutathione S-transferase and His-Tag affinity ligands, respectively). The expression vector can be introduced into a suitable host cell for expression. Host cells are lysed and the lysate, containing fusion protein, can be bound to a suitable affinity matrix by contacting the lysate with an affinity matrix under conditions sufficient for binding of the affinity ligand portion of the fusion protein to the affinity matrix.

In one embodiment, the fusion protein can be immobilized on a suitable affinity matrix under conditions sufficient to bind the affinity ligand portion of the fusion protein to the matrix, and is contacted with one or more candidate biomolecules (e.g., a mixture of peptides) to be tested as biomolecular binders, under conditions suitable for binding of the biomolecules to the target portion of the bound fusion protein. Next, the affinity matrix with bound fusion protein can be washed with a suitable wash buffer to remove unbound biomolecules and non-specifically bound biomolecules. Biomolecules which remain bound can be released by contacting the affinity matrix with fusion protein bound thereto with a suitable elution buffer. Wash buffer can be formulated to permit binding of the fusion protein to the affinity matrix, without significantly disrupting binding of specifically bound biomolecules. In this aspect, elution buffer can be formulated to permit retention of the fusion protein by the affinity matrix, but can be formulated to interfere with binding of the test biomolecule(s) to the target portion of the fusion protein. For example, a change in the ionic strength or pH of the elution buffer can lead to release of biomolecules, or the elution buffer can comprise a release component or components designed to disrupt binding of biomolecules to the target portion of the fusion protein.

Immobilization can be performed prior to, simultaneous with, or after contacting the fusion protein with biomolecule, as appropriate. Various permutations of the method are possible, depending upon factors such as the biomolecules tested, the affinity matrix-ligand pair selected, and elution buffer formulation. For example, after the wash step, fusion protein with biomolecules bound thereto can be eluted from the affinity matrix with a suitable elution buffer (a matrix elution buffer, such as glutathione for a GST fusion). Where the fission protein comprises a cleavable linker, such as a thrombin cleavage site, cleavage from the affinity ligand can release a portion of the fusion with the biomolecules bound thereto. Bound biomolecule can then be released from the fusion protein or its cleavage product by an appropriate method, such as extraction.

One or more candidate biomolecular binders can be tested simultaneously. Where a mixture of biomolecules is tested, the biomolecules selected by the foregoing processes can be separated (as appropriate) and identified by suitable methods (e.g., PCR, sequencing, chromatography). Large libraries of biomolecules (e.g., peptides, RNA oligonucleotides) produced by combinatorial chemical synthesis or other methods can be tested (see e.g., Ohlmeyer, M. H. J. et al., *Proc. Natl. Acad. Sci. USA* 90:10922–10926 (1993) and DeWitt, S. H. et al., *Proc. Natl. Acad. Sci. USA* 90:6909–6913 (1993), relating to tagged compounds; see also Rutter, W. J. et al. U.S. Pat. No. 5,010,175; Huebner, V. D. et al., U.S. Pat. No. 5,182,366; and Geysen, H. M., U.S. Pat. No. 4,833,092). Random sequence RNA libraries (see Ellington, A. D. et al., *Nature* 346:818–822 (1990); Bock, L. C. et al., *Nature* 355:584–566 (1992); and Szostak, J. W., *Trends in Biochem. Sci.* 17:89–93 (March, 1992)) can also be screened according to the present method to select RNA molecules which bind to a target. Where biomolecules selected from a combinatorial library by the present method carry unique tags, identification of individual biomolecules by chromatographic methods is possible. Where biomolecules do not carry tags, chromatographic separation, followed by mass spectrometry to ascertain structure, can be used to identify individual biomolecules selected by the method, for example.

Other methods to identify biomolecular binders of a target cell component can be used. For example, the two-hybrid system or interaction trap is an in vivo system that can can be used to identify polypeptides, peptides or proteins (candidate biomolecular binders) that bind to a target protein. In this system, both candidate biomolecular binders and target cell component proteins are produced as fusion proteins. The two-hybrid system and variations on it have been described (U.S. Pat. No. 5,283,173 and U.S. Pat. No. 5,468,614; Golemis, E. A. et al., pages 20.1.1–20.1.35 In *Current Protocols in Molecular Biolog*, F. M. Ausubel et al., eds., John Wiley and Sons, containing supplements up through Supplement 40, 1997; two-hybrid systems available from Clontech, Palo Alto, Calif.).

Once one or more biomolecular binders of a cell component have been identified, further steps can be combined with those taken to identify the biomolecular binder, to identify those biomolecular binders that produce a phenotypic effect on a cell (where "a cell" can mean cells of a cell strain or cell line). Thus, a method for identifying a biomolecule that produces a phenotypic effect on a first cell can comprise the steps of identifying a biomolecular binder of an isolated target cell component of the first cell; constructing a second cell comprising the target cell component and a regulable exogenous gene encoding the biomolecular binder; and testing the second cell for the phenotypic effect, upon production of the biomolecular binder in the second cell, where the second cell can be maintained in culture or introduced into an experimental animal. If the second cell shows the phenotypic effect upon intracellular production of the biomolecular binder, then a biomolecule that produces a phenotypic effect on the first cell has been identified. Testing the second cell is general step (2) of the invention, as the three general steps were outlined above.

Host cells (also, "second cells" in the terminology used above) of the cell type (e.g., species of pathogenic bacteria) the target was isolated from (or the gene encoding the target was originally isolated from, if the target is produced by recombinant methods), can be engineered to harbor a gene that can regulably express the biomolecular binder (e.g., under an inducible or repressible promoter). The ability to regulate the expression of the biomolecular binder is desirable because constitutive expression of the biomolecular binder could be lethal to the cell. Therefore, inducible or regulated expression gives the researcher the ability to control if and when the biomolecular binder is expressed. The gene expressing the biomolecular binder can be present in one or more copies, either on an extrachromosomal structure, such as on a single or multicopy plasmid, or integrated into the host cell genome. Plasmids that provide an inducible gene expression system in pathogenic organisms can be used. For example, plasmids allowing tetracycline-inducible expression of a gene in *Staphylococcus aureus* have been developed. See Example 6.

For intracellular expression of a biomolecule to be tested for its phenotypic effect in a eukaryotic cell (e.g., mammalian cell), the genes for expression can be carried on plasmid-based or virus-based vectors, or on a linear piece of DNA or RNA. For examples of expression vectors, see Hosfield and Lu, *Biotechniques* 25:306–309, 1998; Stephens and Cockett, *Nucleic Acid Research* 17:7110, 1989; Wohlgemuth et al, *Gene Therapy* 3:503–512, 1996; Ramirez-Solis et al, *Gene* 87:291–294, 1990; Dirks et al, *Gene* 149:387–388, 1994; Chengalvala et al. *Current Opinion in Biotechnologies* 2:718–722, 1991; *Methods in Enzymology*, Volume 185, (D. V. Goeddel, ed.) Academic Press, San Diego, 1990. The genetic material can be introduced into cells using a variety of techniques, including whole cell or protoplast transformation, electroporation, calcium phosphate-DNA precipitation or DEAE-Dextran transfection, liposome mediated DNA or RNA transfer, or transduction with recombinant viral or retroviral vectors. Expression of the gene can be constitutive (e.g., ADH1 promoter for expression in *S. cerevisiae* (Bennetzen, J. L. and Hall, B. D., *J. Biol. Chem.* 257:3026–3031 (1982)), or CMV immediate early promoter and RSV LTR for mammalian expression) or inducible, as the inducible GAL1 promoter in yeast (Davis, L. I. and Fink, G. R., Cell 61:965–978 (1990)). A variety of inducible systems can be utilized, for example, *E. coli* Lac repressor/operator system and Tn10 Tet repressor/operator systems have been engineered to govern regulated expression in organisms from bacterial to mammalian cells. Regulated gene expression can also be achieved by activation. For example, gene expression governed by HIV LTR can be activated by HIV or SIV Tat proteins in human cells; GAL4 promoter can be activated by galactose in a nonglucose-containing medium. The location of the biomolecule binder genes can be extrachromosomal or chromosomally integrated. The chromosome integration can be mediated through homologous or nonhomologous recombinations.

For proper localization in the cells, it may be desirable to tag the biomolecule binders with certain peptide signal sequences (for example, nuclear localization signal (NLS) sequences, mitochondria localization sequences). Secretion sequences have been well documented in the art.

For presentation of the biomolecular binders in the intracellular system, they can be fused N-terminally, C-terminally, or internally in a carrier protein (if the biomolecular binder is a peptide), and can be fused (5', 3' or internally) in a carrier RNA or DNA molecule (if the biomolecular binder is a nucleic acid). The biomolecular binder can be presented With a protein or nucleic acid structural scaffold. Certain linkages (e.g., a 4-glycine linker for a peptide or a stretch of A's for an RNA can be inserted between the biomolecular binder and the carrier proteins or nucleic acids.

In such engineered cells, the effect of this biomolecular binder on the phenotype of the cells can be tested, as a manifestation of the binding (implying binding to a functionally relevant site, thus, an activator, or more likely, an inhibitory) effect of the biomolecular binder on the target used in an in vitro binding assay as described above. An intracellular test can not only determine which biomolecular binders have a phenotypic effect on the cells, but at the same time can assess whether the target in the cells is essential for maintaining the normal phenotype of the cells. For example, a culture of the engineered cells expressing a biomolecular binder can be divided into two aliquots. The first aliquot ("test" cells) can be treated in a suitable manner to regulate (e.g., induce or release repression of, as appropriate) the gene encoding the biomolecular binder, such that the biomolecular binder is produced in the cells. The second aliquot ("control" cells) can be left untreated so that the biomolecular binder is not produced in the cells. In a variation of this method of testing the effect of a biomolecular binder on the phenotype of the cells, a different strain of cells, not having a gene that can express the biomolecular binder, can be used as control cells. The phenotype of the cells in each culture ("test" and "control" cells grown under the same conditions, other than the expression of the biomolecular binder), can then be monitored by a suitable means (e.g., enzymatic activity, monitoring a product of a biosynthetic pathway, antibody to test for presence of cell surface antigen, etc.). Where the change in phenotype is a change in growth rate, the growth of the cells in each culture ("test" and "control" cells grown under the same conditions, other than the expression of the biomolecular binder), can be monitored by a suitable means (e.g., turbidity of liquid cultures, cell count, etc). If the extent of growth or rate of growth of the test cells is less than the extent of growth or rate of growth of the control cells, then the biomolecular binder can be concluded to be an inhibitor of the growth of the cells, or a biomolecular inhibitor.

If the phenotype of the test cells is altered relative to that of the control cells, then the biomolecular binder can be concluded to be one that causes a phenotypic effect. In an optional additional test, isolated target cell component having a known function (e.g., an enzyme activity) can be tested for modulation of this known function in the presence of biomolecular binder under conditions conducive to binding of the biomolecular binder to the target cell component. Positive results in these tests should encourage the investigator to continue in the drug discovery process with efforts to find a more stable compound (than a peptide, polypeptide or RNA biomolecule) that mimics the binding properties of the biomolecular binder on the tested target cell component.

A further test can, again, employ an engineered strain of cells that comprise both the target cell component and one or more genes encoding a biomolecule tested to be a biomolecular binder of the target cell component. The cells of the cell strain can be tested in animals to see if regulable expression of the biomolecular binder in the engineered cells produces an observable or testable change in phenotype of the cells. Both the "in culture" test for the effect of intracellular expression of the biomolecular binder and the "in animal" test (described below) for the effect of intracellular expression of the biomolecular binder can be applied not only towards drug discovery in the categories of antimicrobials and anticancer agents, but also towards the discovery of therapeutic agents to treat inflammatory diseases, cardiovascular diseases, diseases associated with metabolic pathways, and diseases associated with the central nervous system, for example.

Where the engineered strain of cells is a strain of pathogen cells or tumor cells, the object of the test is to see whether production of the biomolecular binder in the engineered strain inhibits growth of these cells after their introduction into an animal by the engineered pathogen. Such a test can not only determine which biomolecular binders are inhibitors of growth of the cells, but at the same time can assess whether the target in the cells is essential for maintaining growth of the cells (infection, for a pathogenic organism) in a host mammal. Suitable animals for such an experiment are, for example, mammals such as mice, rats, rabbits, guinea pigs, dogs, pigs, and the like. Small mammals are preferred for reasons of convenience. The engineered cells are introduced into one or more animals ("test" animals) and into one or more animals in a separate group ("control" animals) by a route appropriate to cause symptoms of systemic or local growth of the engineered cells. The route of introduction may be, for example, by oral feeding, by inhalation, by subdermal, intramuscular, intravenous, or intraperitoneal injection as appropriate to the desired result.

After the cell strain has been introduced into the test and control animals, expression of the gene encoding the biomolecular binder is regulated to allow production of the biomolecular binder in the engineered pathogen cells. This can be achieved, for instance, by administering to the test animals a treatment appropriate to the regulation system built into the cells, to cause the gene encoding the biomolecular binder to be expressed. The same treatment is not administered to the control animals, but the conditions under which they are maintained are otherwise identical to those of the test animals. The treatment to express the gene encoding the biomolecular binder can be the administration of an inducer substance (where expression of the biomolecular binder or gene is under the control of an inducible promoter) or the functional removal of a repressor substance (where expression of the biomolecular binder gene is under the control of a repressible promoter).

After such treatment, the test and control animals can be monitored for a phenotypic effect in the introduced cells. Where the introduced cells are constructed pathogen cells, the animals can be monitored for signs of infection (as the simplest endpoint, death of the animal, but also e.g., lethargy, lack of grooming behavior, hunched posture, not eating, diarrhea or other discharges; bacterial titer in samples of blood or other cultured fluids or tissues). In the case of testing engineered tumor cells, the test and control animals can be monitored for the development of tumors or for other indicators of the proliferation of the introduced engineered cells. If the test animals are observed to exhibit less growth of the introduced cells than the control animals, then the biomolecule can be also called a biomolecular inhibitor of growth, or biomolecular inhibitor of infection, as appropriate, as it can be concluded that the expression in vivo of the biomolecular inhibitor is the cause of the relative reduction in growth of the introduced cells in the test animals.

Further steps of the procedure involve in vitro assays to identify one or more compounds that have binding and activating or inhibitory properties that are similar to those of the biomolecules which have been found to have a phenotypic effect, such as inhibition of growth. That is, compounds that compete for binding to a target cell component with the biomolecule would then be structural analogs of the biomolecules. Assays to identify such compounds can take advantage of known methods to identify competing molecules in a binding assay. These steps comprise general step (3) of the method.

In one method to identify such compounds, a biomolecular inhibitor (or activator) can be contacted with the isolated target cell component to allow binding, one or more compounds can be added to the milieu comprising the biomolecular inhibitor and the cell component under conditions that allow interaction and binding between the cell component and the biomolecular inhibitor, and any biomolecular inhibitor that is released from the cell component can be detected.

One suitable system that allows the detection of released biomolecular inhibitor (or activator) is one in which fluorescence polarization of molecules in the milieu can be measured. The biomolecular inhibitor can have bound to it a fluorescent tag or label such as fluorescein or fluorescein attached to a linker. Assays for inhibition of the binding of the biomolecular inhibitor to the cell component can be done in microtiter plates to conveniently test a set of compounds at the same time. In such assays, a majority of the fluorescently labeled biomolecular inhibitor must bind to the protein in the absence of competitor compound to allow for the detection of small changes in the bound versus free probe population when a compound which is a competitor with a biomolecular inhibitor is added (B. A. Lynch, et al., *Analytical Biochemistry* 247:77–82 (1997)). If a compound competes with the biomolecular inhibitor for a binding site on the target cell component, then fluorescently labeled biomolecular inhibitor is released from the target cell component, lowering the polarization measured in the milieu.

In a further method for identifying one or more compounds that compete with a biomolecular inhibitor (or activator) for a binding site on a target cell component, the target cell component can be attached to a solid support, contacted with one or more compounds, and contacted with the biomolecular inhibitor. One or more washing steps can be employed to remove biomolecular inhibitor and compound not bound to the cell component. Either the biomolecular inhibitor bound to the target cell component or the compound bound to the target cell component can be measured. Detection of biomolecular inhibitor or compound bound to the cell compound can be facilitated by the use of a label on either molecule type, wherein the label can be, for instance, a radioactive isotope either incorporated into the molecule itself or attached as an adduct, streptavidin or biotin, a fluorescent label or a substrate for an enzyme that can produce from the substrate a colored or fluorescent product. An appropriate means of detection of the labeled biomolecular inhibitor or compound moiety of the biomolecular inhibitor-cell component complex or the compound-cell component complex can be applied. For example, a scintillation counter can be used to measure radioactivity. Radiolabeled streptavidin or biotin can be allowed to bind to biotin or streptavidin, respectively, and the resulting complexes detected in a scintillation counter. Alkaline phosphatase conjugated to streptavidin can be added to a biotin-labeled biomolecular inhibitor or compound. Detection and quantitation of a biotin-labeled complex can then be by addition of pNPP substrate of alkaline phosphatase and detection by spectrophotometry, of a product which absorbs UV light at a wavelength of 405 nm. A fluorescent label can also be used, in which case detection of fluorescent complexes can be by a fluorometer. Models are available that can read multiple samples, as in a microtiter plate.

For example, in one type of assay, the method for identifying compounds comprises attaching the target cell component to a solid support, contacting the biomolecular inhibitor with the target cell component under conditions suitable for binding of the biomolecular inhibitor to the cell component, removing unbound biomolecular inhibitor from the solid support, contacting one or more compounds (e.g., a mixture of compounds) with the cell component under conditions suitable for binding of the biomolecular inhibitor to the cell component, and testing for unbound biomolecular inhibitor released from the cell component, whereby if unbound biomolecular inhibitor is detected, one or more compounds that displace or compete with the biomolecular inhibitor for a particular site on the target cell component have been identified.

Other methods for identifying compounds that are competitive binders with the biomolecule for a target can employ adaptations of fluoresence polarization methods. See, for instance, *Anal. Biochem.* 253(2):210–218 (1997), *Anal. Biochem.* 249(1):29–36 (1997), *BioTechniques* 17(3):585–589 (1994) and *Nature* 373:254–256 (1995).

Those compounds that bind competitively to the target cell component can be considered to be drug candidates. Further appropriate testing can confirm that those compounds which bind competitively with biomolecular inhibitors (or activators) possess the same activity as seen in an intracellular test of the effect of the biomolecular inhibitor or activator upon the phenotype of cells. Derivatives of these compounds having modifications to confer improved solubility, stability, etc., can also be tested for a desired phenotypic effect.

Combining steps for testing the phenotypic effects of a biomolecule, as can be produced in an intracellular test, with steps for identifying compounds that compete with the biomolecule for sites on a target cell component, yields a method for identifying a compound which is a functional analog of a biomolecule which produces a phenotypic effect on a cell. These steps can be to test, for the phenotypic effect, either in culture or in an animal model, or in both, a cell which produces a biomolecule by regulable expression of an exogenous gene in the cell, and to identify, if the biomolecule caused the phenotypic effect, one or more compounds that compete with the biomolecule for binding to a target cell component. If a compound is found to compete with the biomolecule for binding to the target cell component, then the compound is a functional analog of a biomolecule which produces a phenotypic effect on the cell. Such a functional analog can cause qualitatively a similar effect on the cell, but to a similar degree, lesser degree or greater degree than the biomolecule.

A further embodiment of the invention combining general steps (1) and (2) is a method for determining whether a target component of a cell is essential to producing a phenotypic effect on the cell, comprising isolating the target component from the cell, identifying a biomolecular binder of the isolated target component of the cell, constructing a second cell comprising the target component and a regulable, exogenous gene encoding the biomolecular binder, and testing the second cell in culture for an altered phenotypic effect, upon production of the biomolecular binder in the second cell, whereby, if the second cell shows the altered phenotypic effect upon production of the bimolecular binder, then the target component of the first cell is essential to producing the phenotypic effect on the first cell.

The methods described herein are well suited to the identification of compounds that can inhibit the proliferation of the cells of infectious agents such as bacteria, fungi and the like. In addition, a procedure such as the one outlined below can be used in the identification of compounds to inhibit the proliferation of cancer cells. The two procedures described below further illustrate the use of the methods described herein and would provide proof of principle of these methods with a known target for anticancer therapy.

Mammalian dihydrofolate reductase (DHFR) is a proven target for anticancer therapy. Methotrexate (MTX) is one of many existing drugs that inhibit DHFR. It is widely used for anticancer chemotherapy.

NIH 3T3 is a mouse fibroblast cell line that is able to develop spontaneous transformed cells when cultured in low concentration (2%) of calf serum in molecular, cellular and developmental biology medium 402 (MCDB) (M. Chow and H. Rubin, Proc. Natl. Acad. Sci. USA 95(8):45504555 (1998)). The transformed cells, which can be selectively inhibited by MTX (Chow and Rubin), are isolated. Both the normal and transformed NIH3T3 cells are transfected with pTet-On plasmid (Clontech; Palo Alto, Calif.). Stable cell lines that express high levels of reverse tetracycline-controlled activator (rtTA) are isolated and characterized for their normal or transformed phenotype (Chow and Rubin).

The DHFR gene (Genbank Accession #L26316) from the NIH 3T3 cell line is amplified by reverse transcription-PCR (RT-PCR) using poly $A^+$RNA isolated from NIH 3T3 cells (Sambrook, J. et al., *Molecular Cloning: A Laboratory Manual,* 2nd edition, Cold Spring Harbor Laboratory Press, 1989). Active DHFR is expressed using the BacPAK Baculovirus Expression System (Clontech) or other appropriate systems. The expressed DHFR is purified and biotinylated and subjected to peptide binder identification as exemplified for bacterial proteins. The identified peptides are biochemically characterized for in vitro inhibition of DHFR activity. Peptides that inhibit DHFR are identified. A nucleic acid encoding each peptide can be cloned into a vector such as pGEX-4T2 (Pharmacia) to yield a vector which encodes a fusion polypeptide having the peptide fused to the N-terminus of GST. This can also be done by PCR amplification as exemplified herein for the peptide Pro-3. The fusion genes are cloned into plasmid pTRE (Clontech) for regulated expression. The constructed plasmid or the vector is cotransfected with pTK-Hyg into the stable NIH 3T3 cell line that expresses rtTA. The resulting cell lines, termed 3T3N-VITA (normal 3T3 cells that express rtTA and the DHFR inhibitory peptides), 3T3T-VITA (transform ed 3T3 cells that express rtTA and the DHFR inhibitory peptides), or 3T3T-VITA control (transformed 3T3 cells that express rtTA and GST), are characterized for their normal or transformed phenotype (loss of contact inhibition, change in morphology, immortalization, etc.).

$10^2$–$10^3$ of 3T3T-VITA or 3T3T-VITA control cells are mixed with $10^5$ 3T3N-VITA and are grown in MCDB 402 medium with 10% calf serum at 37° C. for three days. Tetracycline is added to the medium to a final concentration of 0 to 1 $\mu$g/ml. In a control, 200 nM of MTX is added. The cultures are incubated for an additional eight days, and the number of foci formed are counted as described by M. Chow and H. Rubin, Proc. Natl. Acad. Sci. USA 95(8):45504555 (1998). Peptides that specifically inhibit foci formation of 3T3 transformed cells are identified.

A murine model of fibroblastoma (Kogerman, P. et al., *Oncogene.* 15(12):1407–1416 (1997)) is used for evaluting the DHFR/peptide combination for identification of compounds for cancer therapy. Various amounts of 3T3T-VITA or 3T3T-VITA control cells ($10^3$, $10^4$, $10^5$, $10^6$ cells) are injected subcutaneously into 5 groups (10 in each group) of athymic nude mice (46 weeks old, 18–22 g) to determine the minimal dose needed for development of fibroblastomas in all of the tested animals. Upon determination of the minimal tumorigenic dose, 6 groups of athymic nude mice (10 each) are injected subcutaneously (s.c.) with the minimal tumorigenic dose for 3T3T-VITA or 3T3T-VITA control cells to develop fibroblastoma. One week after injection, group 1 mice start receiving MTX s.c. at 2 mg/kg/day as positive control, group 2 to 5 start receiving 1, 2, 5, or 10 mg/kg/day of tetracycline, group 6 start receiving saline (vehicle) as control. Five weeks after the introduction of cells, all of the mice are sacrificed and tumors are removed from them. Tumor mass is measured and compared among the groups.

An effective peptide identified by these in vivo experiments can be used for screening libraries of compounds to identify those compounds that competitively bind to DHFR.

One mechanism of tumorigenesis is overexpression of proto-oncogenes such as Ha-ras (Reviewed by Suarez, H. G., *Anticancer Research* 9(5):1331–1343 (1989)). Compounds that inhibit the activities of the products of such proto-oncogenes can be used for cancer chemotherapy. What follows is a further illustration of the methods described herein, as applied to mammalian cells.

Transgenic mice that overexpress human Ha-ras have been produced. Such transgenic mice develop salivary and/ or mammary adenocarcinomas (Nielsen, L. L. et al, In Vivo 8(5):1331–1343 (1994)). Secondary transgenic mice that express rtTA can be generated using the pTet-On plasmid from Clontech.

Human Ha-ras open reading frame cDNA (Genbank Accession #G00277) is amplified by RT-PCR using polyA⁻ RNA isolated from human mammary gland or other tissues. Active Ha-ras is expressed using the BacPAK Baculovirus Expression System (Clontech) or other appropriate systems. The expressed Ha-ras is purified and biotinylated and subjected to peptide binder identification as exemplified herein for bacterial proteins as target cell components. The identified peptides are biochemically characterized for in vitro inhibition of Ha-ras GTPase activity. Peptides that inhibit Ha-ras are cloned into plasmid pTRE (Clontech) for regulated expression as an N-terminal fusion of GST. Such constructs are used to generate tertiary transgenic mice using the secondary transgenic mice. Transgenic mice that are able to overexpress peptide genes are identified by Northern and Western analysis. Control mice that express GST are also identified.

Various doses of tetracycline are administered to the tertiary transgenic mice by s.c. or i.p. injection before or after tumor onset. Prevention or regression of tumors resulting from expression of the peptide genes are analyzed as described above for murine fibroblastoma.

Peptides found to be effective in in vivo experiments will be used to screen compounds that inhibit human Ha-ras activity for cancer therapy.

The method of the invention can be applied more generally to mammalian diseases caused by: (1) loss or gain of protein function, (2) over-expression or loss of regulation of protein activity. In each case the starting point is the identification of a putative protein target or metabolic pathway involved in the disease. The protocol can sometimes vary with the disease indication, depending on the availability of cell culture and animal model systems to study the disease. In all cases the process can deliver a validated target and assay combination to support the initiation of drug discovery.

Appropriate disease indications include, but are not limited to, Alzheimer's, arthritis, cancer, cardiovascular diseases, central nervous system disorders, diabetes, depression, hypertension, inflammation, obesity and pain.

Appropriate protein targets putatively linked to disease indications include, but are not limited to (1) the leptin protein, putatively linked to obesity and diabetes; (2) a mitogen-activated protein kinase putatively linked to arthritis, osteoporosis and atherosclerosis; (3) the interleukin-1 beta converting protein putatively linked to arthritis, asthma and inflammation; (4) the caspase proteins putatively linked to neurodegenerative diseases such as Alzheimer's, Parkinson's and stroke, and (5) the tumor necrosis factor protein putatively linked to obesity and diabetes. Appropriate protein targets include also, but are not limited to, enzymes catalyzing the following types of reactions: (1) oxido-reductases, (2) transferases, (3) hydrolases, (4) lyases, (5) isomerases, and (6) ligases.

The arachidonic acid pathway constitutes one of the main mechanisms for the production of pain and inflammation. The pathway produces different classes of end products, including the prostaglandins, thromboxane and leukotrienes. Prostaglandins, an end product of cyclooxygenase metabolism, modulate immune function, mediate vascular phases of inflammation and are potent vasodilators. The major therapeutic action of aspirin and other non-steroidal anti-inflammatory drugs (NSAIDs) is proposed to be inhibition of the enzyme cyclooxygenase (COX). Anti-inflammatory potencies of different NSAIDs have been shown to be proportional to their action as COX inhibitors. It has also been shown that COX inhibition produces toxic side effects such as erosive gastritis and renal toxicity. The knowledge base regarding the toxic side effects of COX inhibitors has been gained through years of monitoring human therapies and human suffering. Two kinds of COX enzymes are now known to exist, with inhibition of COX1 related to toxicity, and inhibition of COX2 related to reduction of inflammation. Thus, selective COX2 inhibition is a desirable characteristic of new anti-inflammatory drugs. The method of the invention can provide a route from identification of potential drug targets to validating these targets (for example, COX1 and COX2) as playing a role in disease (pain and inflammation) to an examination of the phenotype for the inhibition of one or both target isozymes without human suffering. Importantly, this information can be collected in vivo.

As an alternative strategy, the method of the invention can be used to define the phenotype of "genes of unknown function" obtained from various human genome sequencing projects or to assess the phenotype resulting from inhibition of one isozyme subtype or one member of a family of related protein targets.

The present invention is more specifically illustrated in the following examples, which are not intended to be limiting in any way.

EXEMPLIFICATION

Example 1

Isolating a Peptide that Binds to and Inhibits E. coli Prolyl-tRNA Synthetase

Because of its well established genetic and expression systems, Escherichia coli was chosen for initial tests of the methods. Prolyl-tRNA synthetase (ProRS) catalyzes the attachment of proline to its cognate tRNA for protein biosynthesis. It is an enzyme of essential cellular function and is a good candidate for target validation.

In order to produce pure protein for peptide selection, the E. coli ProRS gene (Genbank accession number: M97858) was PCR amplified and cloned into the pET-20b vector (Novagen) using standard molecular cloning protocols (J. Sambrook, et al., *Molecular Cloning: A Laboratory Manual, 2nd edition*, Cold Spring Harbor Laboratory Press, 1989). The overexpressed ProRS was purified sequentially on Q- and SP-Sepharose columns. The purified ProRS was biotinylated using EZ-link™ Sulfo-NHS-LC-Biotin from Pierce according to the instructions packaged with the biotinylation compound, captured onto streptavidin-agarose beads and used to select specific binding peptides from a peptide library displayed on coat protein III of M13 phages using a standard protocol (J. K. Scott and G. P. Smith, Science 249:386390 (1990)). Thirteen clones from phages that were identified as having a high affinity to ProRS were sequenced. These clones share 4 different sequences, 3 of which are closely related (Table 1). See Example 4 of WO98/19162, published 7 May 1998.

TABLE 1

| | Peptide sequences with high binding affinity to E. Coli ProRS | |
|---|---|---|
| SEQ ID NO: | Peptide Sequence | # of Phage Isolated |
| 1 | SRDWGFWDWGVDRSR | 5 |
| 2 | SRDWGFWRLPESMASR | 3 |
| 3 | SREWHFWRDYNPTSR | 4 |
| 4 | SSERGSGDRGEKGSR | 1 |

The peptide having sequence number 3 was synthesized and tested for inhibition of tRNA charging activity of E. coli ProRS. This peptide inhibits E. coli ProRS aminoacylation activity, demonstrates competitive inhibition with both pro-line and ATP, and exhibits a K, of 300 nM. This peptide is called Pro-3 (also, Pro3).

Example 2

Regulated Expression of Pro-3 in E. coli Causes Cessation of Cell Growth

Regulated intracellular expression of the Pro-3 peptide in E. coli was achieved by fusing an oligonucleotide encoding the peptide to the 5' end of a gene encoding a glutathione S-transferase (GST) protein. To generate the peptide expression construct, the Pro-3/GST fusion gene was PCR amplified using a combination of the Pro3, Pro3/GST, and GST/R primers as illustrated in FIG. 1. Primers Pro3 and Pro3/GST encode the Pro-3 peptide sequence; the latter anneals to the 5' end of the GST gene on plasmid pGEX-4T2 (Pharmacia). A 4-amino acid linker was introduced between the Pro-3 peptide and GST for flexibility. The PCR product was further amplified with primers Pro3(Kpn) and GST/R(Bam), digested with KpnI and BamnHI restriction endonucleases, and ligated to the KpnI/BamrI sites of the expression vector pPROTet (Clontech, Palo Alto, Calif.) using standard cloning protocols. pPROTet uses the PL promoter of phage lambda combined with the Tet operator of the Tn10 tetracycline resistance operon to direct the regulated expression of the cloned gene (Clontech, PROTM Bacterial Expression System User Manual, PT3161-1, Version PR7Y629). The ligated DNA was then used to transform DH5αPRO (Clontech), an E. coli strain expressing the Tet repressor. Clone $pC^3 844$ was sequenced and identified as containing the Pro-3/GST fusion gene. The linker between the Pro3 peptide and GST is Glu-Gly-Gly-Gly (SEQ ID NO:18). $pC^3 844$ was also transformed into the E. coli strain JM109/pSC, which is JM109 harboring a plasmid expressing Tet repressor that was isolated from BL21PRO (Clontech). The resulting E. coli strain is called JM109/pSC/$pC^3 844$.

TABLE 2

Oligonucleotides used to generate
Pro-3/GST expression construct

Pro3: 5'CCAACAACATATGTCCCGTGAATGGCACTTCTGGCGTGA-CTAC (SEQ ID NO: 5)
Pro3/GST: 5' TTCTGGCGTGACTACAACCCGACCTCCCGTGGGGGT-GGAGGCATGTCCCCTATACTA (SEQ ID NO: 6)
GST/R: 5'AGTTGAATTCTTAATCCGATTTTGGAGGATGG (SEQ ID NO: 7)
Pro(Kpn): 5'CAAGGTACCCATGTCCCGTGAATGGCAC (SEQ ID NO: 8)
GST/R(Bam): 5'CGCGGATCCTTAATCCGATTTTGGAGGATGG (SEQ ID NO: 9)

Figure 2:
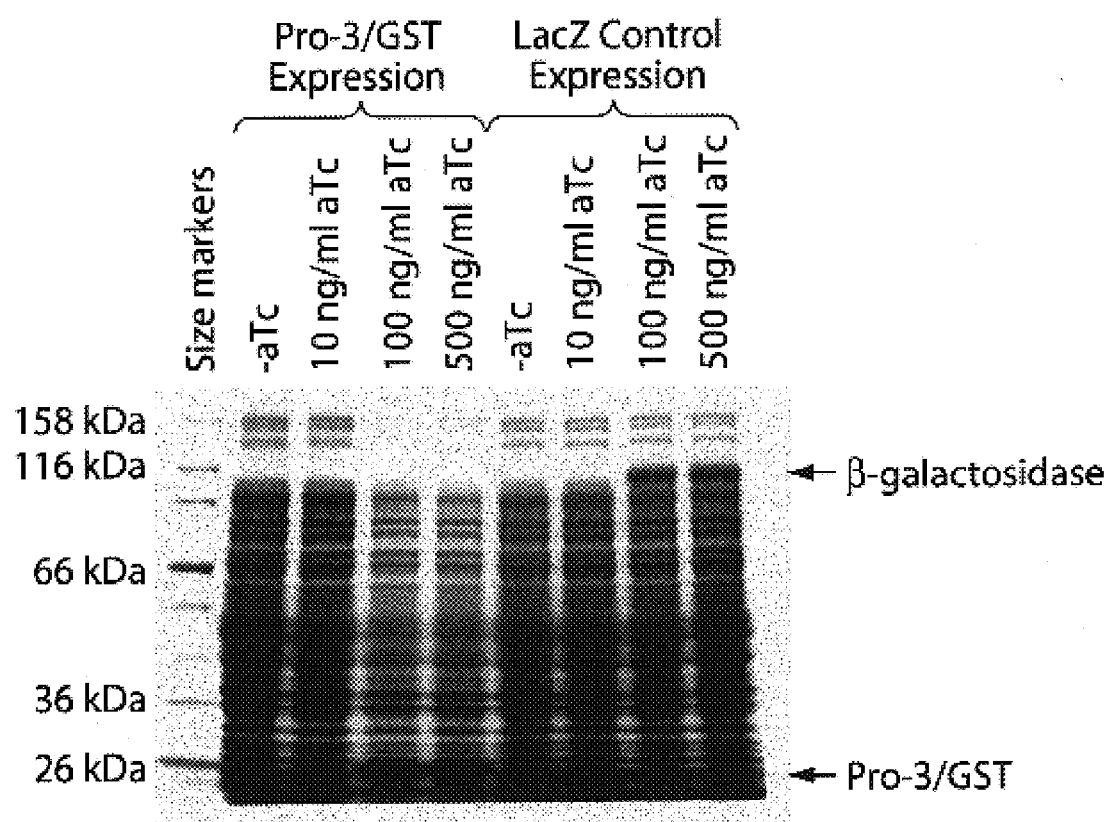
FIG. 2 is a photograph of an SDS-polyacrylamide gel showing expression of the Pro-3 peptide in *E. coli* cells. Production of the Pro-3/GST fusion and production of β-galactosidase in *E. coli* cells carrying pC$^3$844 or pPROTet-LacZ were analyzed by SDS-PAGE. The concentrations of anhydrotetracycline (aTc) used for induction of gene expression are indicated above the lanes on the gel. See Example 2.

To test the expression of the Pro-3/GST fusion gene, overnight cultures of DH5αPRO harboring pC$^3$844 or pPROtet-LacZ (Clontech), a control expression plasmid with the same backbone as pC$^3$844 and a LacZ gene for expression, were inoculated into fresh LB broth containing 34 μg/mL chloramphenicol (an antibiotic for maintaining the expression plasmid), and 50 light spectinomycin (an antibiotic for maintaining the Tet repressor gene). Expression was induced by addition of anhydrotetracycline to 0, 10, 100, or 500 ng/mL, when the bacterial culture reached an OD$_{600}$ of 0.5. Anhydrotetracycline is a derivative of tetracycline that acts as a potent inducer of the TetO/R system and is less toxic to *E. coli* than tetracycline (T. Lederer, et al., *Biochemistry*, 35:7439–7446 (1996); B. Oliva, et al., *Antimicrob. Agents Chemother.* 36:913–919 (1992). After 2.5 hours of induction by exposure to anhydrotetracycline, cells were pelleted from 1 mL culture and lysed by boiling in 100 μL of SDS-PAGE sample buffer. The samples were examined with SDS-PAGE; gels were stained with Coomassie Blue (FIG. 2). The results demonstrated that while basal level expression is undetectable, the Pro-3/GST fusion protein was produced to a significant level upon anhydrotetracycline induction, a level comparable to P-galactosidase production from lacZ. The reduced amount of total protein in the expression samples of Pro-3/GST but not the LacZ control correlates with the growth inhibition observed during the induction of Pro-3/GST (see below).

The expressed Pro-3/GST fusion protein was purified on a glutathione-agarose affinity column according to a procedure provided by Pharmacia (see, cg., procedures manual from Pharmacia P-L Biochemicals, Inc.: GST Gene Fusion System, regarding use of pGEX expression vectors and glutathione-S-transferase fusion proteins, 1993). The N-terminal sequence of the purified protein was determined by Edman cycles and confirmed to have the expected Pro-3 peptide sequence. The purified Pro-3/GST was also confirmed to inhibit *E. coli* ProRS activity, with a K, of 180 nM, similar to that of the Pro-3 peptide.

Figure 3A:
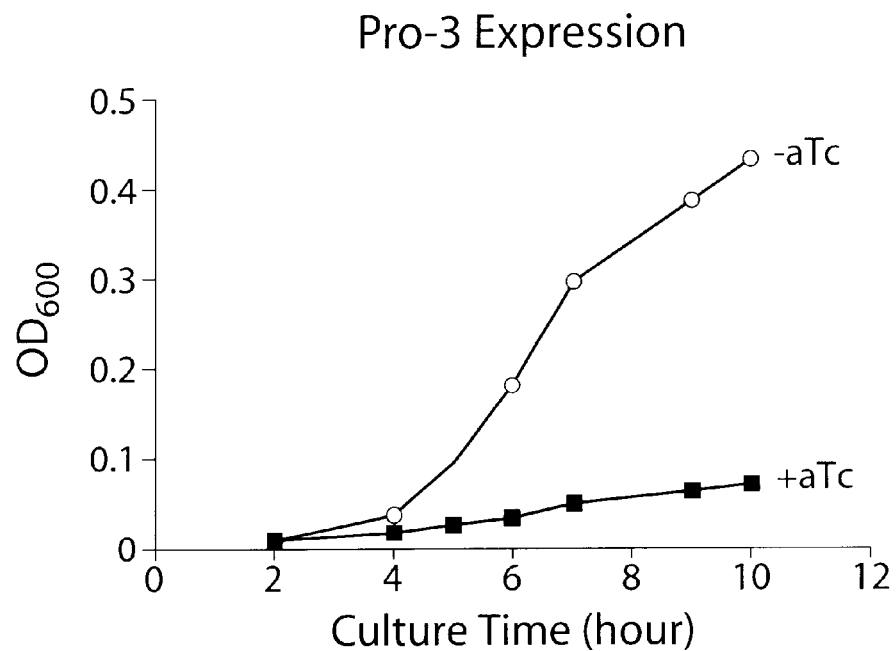
FIG. 3A is a graph showing *E. coli* growth inhibition by expression of Pro-3 peptide encoded on the pC$^3$844 plasmid. The $OD_{600}$ of the bacterial cultures in the presence (+aTc) or absence (−aTc) of anhydrotetracycline were monitored at the time points shown. See Example 2.
Figure 3B:
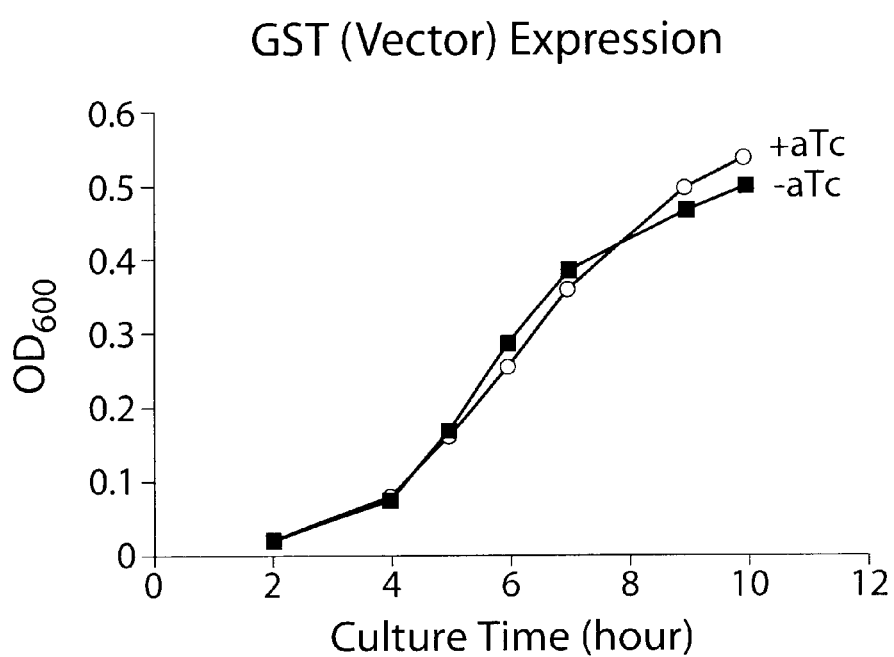
FIG. 3B is a graph showing results of a control experiment to compare with the results shown in FIG. 3A. The *E. coli* cells used in the experiment harbor the pPROTet-GST plasmid.

That expression of Pro-3/GST, but not of GST alone inhibits *E. coli* growth, was demonstrated by the following experiment. Overnight cultures of JM109/pSC cells harboring pC$^3$844 (JM109/pSC/pC$^3$844), or pPROTet-GST (same as pC$^3$844 without the Pro-3 peptide sequence) were diluted 100-fold in fresh LB medium containing 34 μg/mL chloramphenicol and 50 μg/mL spectinomycin. After 2 hours growth at 37° C., 100 μL aliquots of each of these bacterial cultures were transferred to wells of a 96-well microtiter plate, with or without 10 ng of anhydrotetracycline dissolved in 1 μL ethanol. The growth of bacterial cultures, which were constantly under agitation, was monitored with a plate reader (SpectraMAX-250, Molecular Devices). The results depicted in FIG. 3A and FIG. 3B demonstrate that *E. coli* growth was specifically inhibited by expression of the Pro-3 peptide.

Example 3

In vivo Expression of Pro-3 Peptide to Cure a Lethal Infection

Intracellularly expressed Pro-3 was expected to bind to and inhibit a specific essential cellular target in a manner similar to that of an antimicrobial drug. Pro-3 was expected to cure the infection when its expression was induced in an animal model of bacterial infection. An established animal infection model was used to test this concept (C. O. Onyeji et al., *Antimicrob. Agents Chemother.* 38:1112–1117 (1994)).

Eight groups of CD-1 female mice (5 mice per group, Charles River Laboratories; Wilmington, Mass.) weighing 20–24 g were used in this experiment. The inoculum was prepared from *E. coli* JM109/pSC/pC$^3$844 which was cultured at 37° C. for 17 hr in Luria-Bertani broth containing spectinomycin and chloramphenicol, and then 100 μl of the culture was diluted to 1 ml with medium for reading OD at 600 nm (0.2403, the medium as blank). The turbidity of a 0.5 McFarland standard is equivalent to OD$_{600}$0.1, or 10$^8$ cfu/ml. Then 3×10$^9$ cfu (colony-forming units) of *E. coli* JM109/pSC/pC$^3$844 (1.25 ml) from the overnight culture were diluted to 15 ml with 0.01 M phosphate buffered saline (Sigma P-0261) containing 8% hog gastric mucin (Sigma M-2378), 100 μg/ml spectinomycin and 68 μg/ml chloramphenicol. Each mouse of groups 1 through 4 was injected with 0.5 ml of the inoculum intraperitoneally (i.p.), equivalent to 1×10$^8$ cfu/mouse (lethal dose).

Groups 5 through 8 served as vector control. The control inoculum was prepared from *E. coli* pPROTet-GST whose vector carries a gene encoding glutathione S-transferase, but no Pro-3 peptide. *E. coli* pPROTet-GST was cultured at 37° C. for 17 hr in Luria-Bertani broth containing spectinomycin and chloramphenicol, and then 100 μl of the culture were diluted to 1 ml with the medium for reading OD at 600 nm (0.2858, the medium as blank). Then 3×10$^9$ cfu (1.05 ml) from the overnight culture were diluted to 15 ml with 0.01 M phosphate buffered saline containing 8% hog gastric mucin. Each mouse of groups 5 through 8 was injected (i.p.) with *E. coli* pPROTet-GST inocula equivalent to 1×10$^8$ cfu/mouse (lethal dose).

One and four hours after the inoculation, groups 1 and 5 animals received a saline injection i.p. at 10 ml/kg; groups 2, 3 and 4 animals received i.p. injections of anhydrotetracycline at 2, 1 and 0.5 mg/kg (diluted in saline), respectively; groups 6, 7 and 8 received i.p. injections of anhydrotetracycline at 2, 1 and 0.5 mg/kg, respectively. The injection volume for all the animals was 10 ml/kg.

The data summarized in Table 3 demonstrate that inhibition of *E. coli* ProRS activity by in vivo intracellular expression of Pro-3 peptide cures a lethal infection in the mouse model.

TABLE 3

| Group | # of mice | Inoculation | Treatment | Survival (7 days) |
|---|---|---|---|---|
| 1 | 5 | *E. Coli* JM109/pSC/pC$^3$844 10$^8$ cfu/mouse, i.p. | Saline 10 ml/kg, i.p. ×2 | 0/5 |
| 2 | 5 | *E. coli* JM109/pSC/pC$^3$844 10$^8$ cfu/mouse, i.p. | Anhydrotetracycline 2 mg/kg, i.p. ×2 | 5/5 |
| 3 | 5 | *E. coli* JM109/pSC/pC$^3$844 10$^8$ cfu/mouse, i.p. | Anhydrotetracycline 1 mg/kg, i.p. ×2 | 5/5 |

TABLE 3-continued

| Group | # of mice | Inoculation | Treatment | Survival (7 days) |
|---|---|---|---|---|
| 4 | 5 | E. coli JM109/pSC/pC$^3$844 10$^8$ cfu/mouse, i.p. | Anhydro-tetracycline 0.5 mg/kg, i.p. ×2 | 5/5 |
| 5 | 5 | E. coli pPROTet-GST, 10$^8$ cfu/mouse, i.p. | Saline 10 ml/kg, i.p. ×2 | 0/5 |
| 6 | 5 | E. coli pPROTet-GST, 10$^8$ cfu/mouse, i.p. | Anhydro-tetracycline 2 mg/kg, i.p. ×2 | 0/5 |
| 7 | 5 | E. coli pPROTet-GST, 10$^8$ g cfu/mouse, i.p. | Anhydro-tetracycline 1 mg/kg, i.p. ×2 | 0/5 |
| 8 | 5 | E. coli pPROTet-GST, 10$^8$ cfu/mouse, i.p. | Anhydro-tetracycline 0.5 mg/kg, i.p. ×2 | 0/5 |

Example 4

Specific Inhibition of ProRS: Examination of intracellular tRNA charging levels.

The levels of aminoacylated tRNAs in E. coli cells either with or without expression of Pro-3 peptide were examined in order to confirm that E. coli growth inhibition was caused by inhibition of ProRS activity. For this purpose, 400 ml of fresh LB broth containing 34 µg/ml chloramphenicol and 50 µg/ml spectinomycin were inoculated with 4 ml JM109/pSC/pC$^3$844 overnight culture and grown at 37° C. to an OD$_{600}$ of 0.3. The bacterial culture was split into two 200 ml subcultures. To one of them anhydrotetracycline was added to final concentration of 500 ng/ml. After an additional 35 minutes, the bacterial cells were harvested and the level of charged tRNA$^{Pro}$, tRNA$^{Met}$ and tRNA$^{Phe}$ were determined following the protocol described by Folk and Berg (W. R. Folk and P. Berg, Journal of Bacteriology 102:204–212 (1970)). The results as summarized in Table 4 indicate that expression of Pro-3 specifically inhibits charging of tRNA$^{pro}$.

TABLE 4

| | Charged tRNA | |
|---|---|---|
| aaRS | −Inducer | +Inducer |
| ProRS | 70% | 23% |
| MetRS | 108% | 96% |
| PheRS | 104% | 98% |

Example 5

Figure 4A:
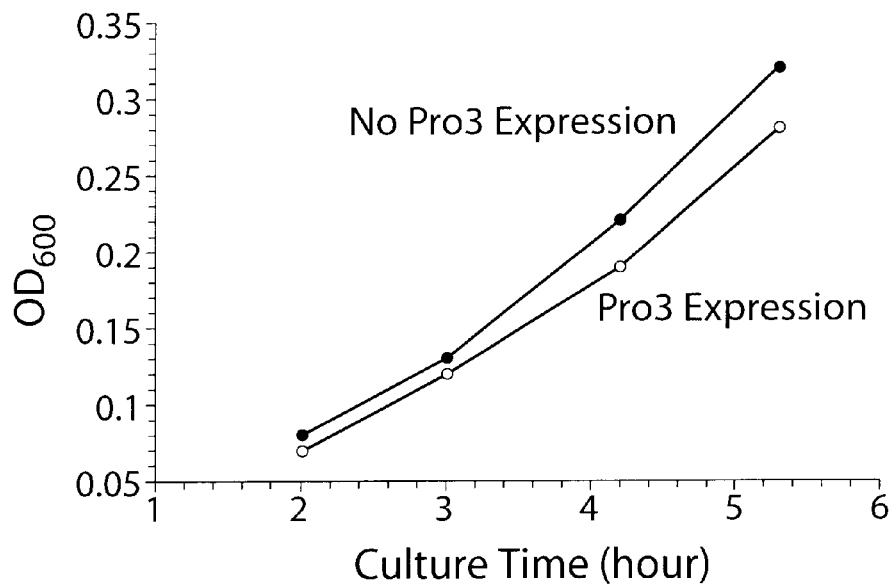
FIG. 4A is a graph showing functional complementation of growth inhibition by Pro-3 peptide, by expression of a heterologous ProRS gene. The growth of *E. coli* cells DH5αPRO/pC$^3$844 carrying a *Staphylococcus aureus* ProRS expression construct was characterized in the presence (Pro3 Expression) or absence (No Pro3 Expression) of 200 ng/ml anhydrotetracycline by monitoring $OD_{60}$, at the time points shown.
Figure 4B:
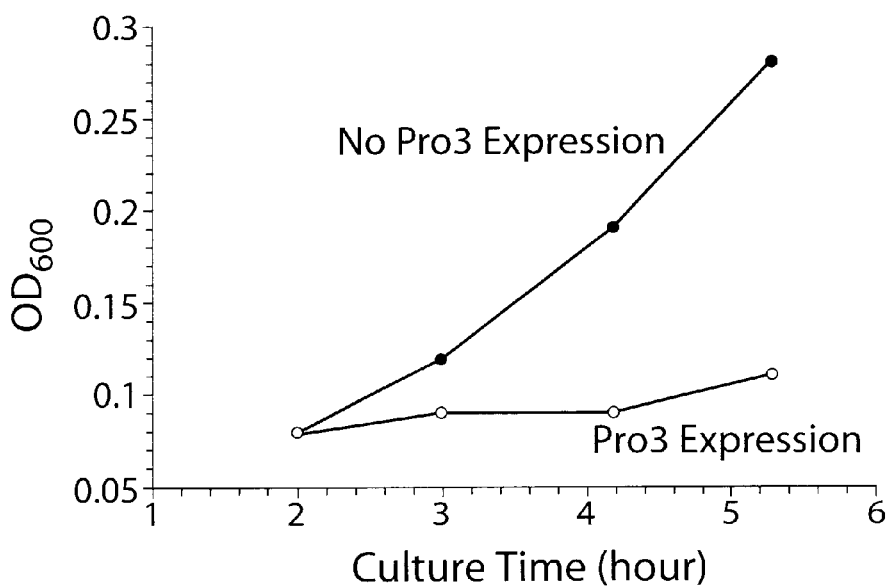
FIG. 4B is a graph showing the results of a control experiment to compare with the results in FIG. 4A. The growth of *E. coli* cells DH5αPRO/pC$^3$844 carrying pACYC 177 was characterized in the presence (Pro3 Expression) or absence (No Pro3 Expression) of 200 ng/ml anhydrotetracycline by monitoring $OD_{600}$ at the time points shown.

Functional Complementation of Pro-3 Peptide Inhibition by Expression of a Heterologous ProRS Gene If ProRS is the primary intracellular target of the Pro-3 peptide, E. coli growth inhibition by Pro-3 peptide should be relieved by functional complementation with a heterologous ProRS. It was found that Pro-3 does not inhibit S. aureus ProRS enzyme activity, which efficiently charges E. coli tRNA$^{Pro}$. The S. aureus ProRS gene (WO 97/26343; EP 785272) was amplified with oligonucleotides S.PRS/XhoI-5' (5'AAT CCG CTC GAG GAT TAT TGC TAT TGG TGC C) (SEQ ID NO: 110) and S.PRS/Hind-3' (5'AAT CGT AAG CTT TTA MTT TAA GTT ATC ATA TTT) (SEQ ID NO:11), digested with Xho I/Hind III restriction endonucleases, and cloned into Xho I/Hind III sites in pACYC177. The cloned S. aureus ProRS gene carries its own promoter and ribosome binding site, and is in the same orientation as the disrupted kanamycin resistance gene in the vector for efficient expression. Either the S. aureus ProRS expression construct or the pACYC177 vector alone was transformed into DH5αPRO/pC$^3$844. The growth of the resulting E. coli strains was followed in the presence or absence of 200 ng/ml anhydrotetracycline. As depicted in FIG. 4A and FIG. 4B, with the S. aureus ProRS expression construct, E. coli cell growth was no longer inhibited by expression of the Pro-3 peptide. The results proved that the growth inhibition by the Pro-3 peptide is specifically caused by inhibition of ProRS activity.

Example 6

S. aureus expression systems

Figure 5:
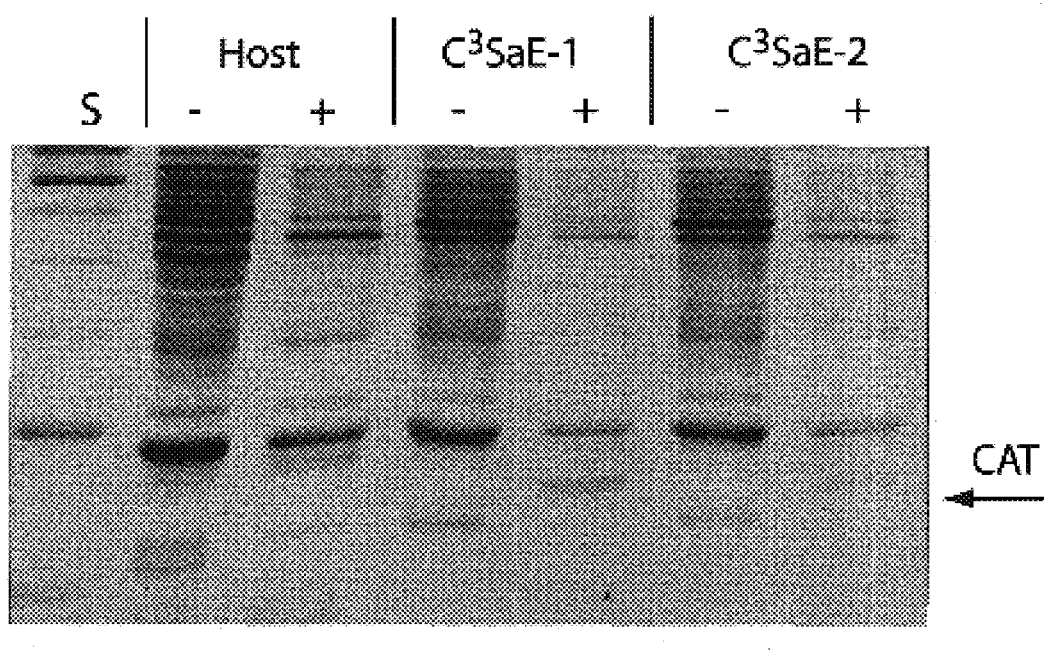
FIG. 5 is a scanned image of an 18% SDS-polyacrylamide gel stained with Coomassie blue. Inducible expression of chloramphenicol acetyltransferase (CAT) in *S. aureus*. The whole cell lysates of *S. aureus* RN4220 (Host) or RN4220 harboring pWH353 (C$^3$SaE-1) or pWH354 (C$^3$SaE-2) with (+) or without (−) tetracycline induction were analyzed by electrophoresis on an 18% SDS-polyacrylamide gel.

E. coli/Bacillus shuttle expression vectors pWH353 and pWH354 were obtained from Professor Wolfgang Hillen (Mikrobielle Genetik, Universität Tübingen, Tübingen, Germany; see M. Geissendörfer and W. Hillen, Appl. Microbiol. Biotechnol., 33:657–663 (1990); DE 3934454). These expression vectors carry a TN10 tet repressor gene. They also contain synthetic promoters with one or two Tet repressor binding sites that are optimized for inducible expression in B. subtilis. These inducible promoters direct the expression of CAT (chloramphenicol acetyltransferase).

pWH353 and pWH354 were transformed into S. aureus RN4220 cells by electroporation (S. Schenk and R. A. Laddaga, CMS Microbiology Letters, 94:133–138 (1992)). The transformants were tested for inducible expression by growing in LB broth containing 30 µg/ml kanamycin. After the OD$_{600}$ reached 0.5, the cultures were split and tetracycline was added to one set of the cultures to a final concentration of 0.5 µg/ml. The cultures were maintained with aeration for 3 hours at 37° C. The S. aureus cells were then pelleted and resuspended in 80 mM Tris-HCl, pH 7.4 containing 200 µg/ml lysostaphin, incubated at 37° C. for 5 minutes, frozen and thawed twice on dry ice/ethanol and 37° C. water bath. The samples were then sonicated twice and centrifuged at 14,000 g for 10 minutes. The supernatants were collected and subjected to electrophoretic analysis on an 18% SDS-polyacrylamide gel stained with Coomassie blue (FIG. 5). The CAT activities in these samples were determined (Frankel, A. D. et al., Proc. Natl. Acad. Sci. USA 86:7397–7401 (1989)) and summarized in Table 5.

TABLE 5

Inducible expression of CAT activity in S. aureus

| Plasmid | Induction | Relative CAT Activity |
|---|---|---|
| No Plasmid | − | ND |
| No Plasmid | + | ND |
| pWH353 | − | 41 |
| pWH353 | + | >4110 |
| pWH354 | − | 1 |
| pWH354 | + | 350 |

ND: Not detectable.

Example 7

Identification of Small Peptides that Specifically Bind to and Inhibit S. aureus Methionyl-tRNA Synthetase (MetRS)

The S. aureus MetRS gene has been cloned (EP 785269; WO 97/26350). The gene was PCR amplified and cloned into pGEX4T2 (Pharmacia) for expression as a GST fusion using standard molecular cloning protocols. The expressed GST-*S. aureus* MetRS was purified on a glutathione agarose column and the GST moiety was removed by thrombin cleavage. The resulting nonfusion *S. aureus* MetRS was then biotinylated using EZ-Link™ Sulfo-NHS-LC-Biotin from Pierce according to the instructions enclosed with the biotinylation compound. The biotinylated *S. aureus* MetRS was used for selecting binding peptides from a 12-mer peptide library displayed on M13 phages (New England Biolabs). After 4 rounds of selection, 12 phage clones were isolated and sequenced. Out of these 12 clones, 11 yielded 4 different sequences as summarized in Table 6. Peptides of sequence JT01 and JT02 were synthesized. JT01 was tested for inhibition of *S. aureus* MetRS activity.

The activity of *S. aureus* MetRS was monitored by the aminoacylation reaction. The enzyme was diluted in 50 mM HEPES, pH 7.55, 5 mM DTT and 0.01% BSA. A typical 50 µL reaction mixture contained 30 mM HEPES, pH 7.5, 10 mM $MgCl_2$, 30 mM KCl, 90 µM *E. coli* tRNA, 2 mM ATP and 5 µM [$^3$H]-methionine (10 Ci/mmol). The reaction was initiated by addition of enzyme at 25° C. At 4 different timepoints, 10 µL of the reaction was quenched into 150 µL cold 5% TCA on a Millipore filter plate. The filter plate is then washed three times with cold 5% TCA followed by water and then ethanol. The filter plate was dried before addition of 100 µL Packard Microscint-20 and counted on a Packard Top-Count microplate scintillation counter.

Inhibition studies were performed for the peptides against two of the substrates, ATP and methionine. This was done at varying concentrations of peptides by holding the concentration of one substrate at its K value (1.5 mM for ATP and 5 µM for methionine), while varying the other substrate concentration around its $K_m$ value. The initial velocity data obtained were then analyzed using GraFit.

Figure 6:
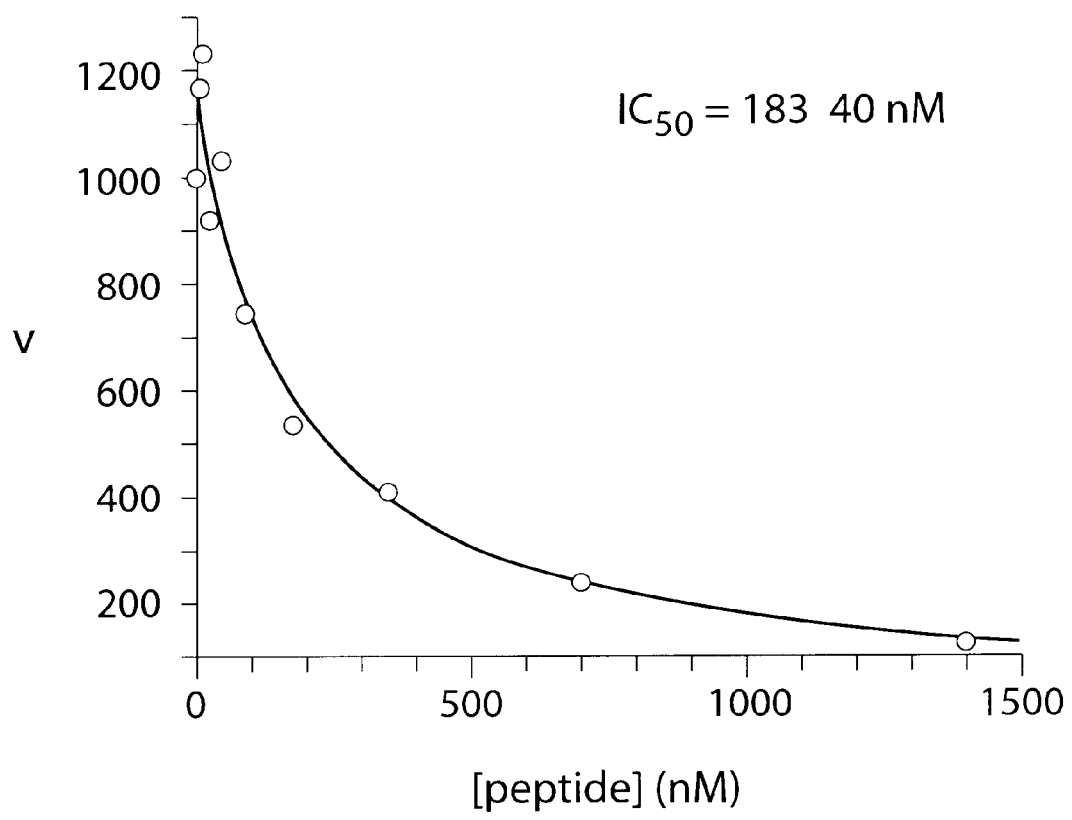
FIG. 6 is a graph showing *S. aureus* MetRS tRNA charging activity (shown as counts per minute of trichloracetic acid precipitable [$^3$H]-methionine) is inhibited by increasing concentrations of JT01.

The results as depicted in FIG. 6 indicate that peptide JT01 is a competitive inhibitor of *S. aureus* MetRS. The $K_i$'s for JT01 are 138 nM (methionine) and 13 nM (ATP). The $K_i$'s for JT02 are 1.7 µM (methionine) and 0.5 µM (ATP) and 13 nM (ATP).

TABLE 6

Peptide sequences identified from phage panning

| Peptide | Peptide Sequence | SEQ ID NO: | Number of Phage Isolated |
| --- | --- | --- | --- |
| JT01 | DPNTWQLRWPMH | 12 | 7 |
| JT02 | MWDLPYIWSRPV | 13 | 2 |
| JT03 | ADTLNWYYYASW | 14 | 1 |
| JT04 | ANNLSTMKKLKQ | 15 | 1 |

Example 8

Development of Assay for *E. coli* ProRS and Pro3 Peptide

A non-radioactive, homogeneous, sensitive Fluorescent Polarization (FP) assay has been developed for *E. coli* ProRS and Pro3 peptide. FP is a ratiometric detection method which is capable of discriminating between free and bound states of a fluorescently labeled tracer based on differences in the rotation rates of the two states. The *E. coli* ProRS FP binding assay involves the incubation of fluorescently labeled Pro3 peptide (Pro3-F) with purified *E. coli* ProRS. In the bound state, Pro3-F is bound to *E coli* ProRS and an increase in ploarization signal is detected using a FP detection system. In the free state, Pro3-F is not bound to *E. coli* ProRS and there is a decrease in polarization signal.

See Example 1 for cloning and purification of *E. coli* ProRS. See Example 1 (SEQ ID NO:3) for description of Pro3 peptide. Fluorescently labeled Pro3 peptide (Pro3-F) was synthesized and purified by SynPep Corp, Dublin, Calif. Its sequence is shown below.

NH2-SREWHFWRDYNPTSRGGK(FITC)-CO-amide (SEQ ID NO:16)

A 96-well plate (Costar cat #3915) was blocked for 1 hour at room temperature with 150 µL/well 2 mg/ml BSA (FisherBiotech cat #BP1600-100) in 0.1 M $NaHCO_3$ The plate was then washed manually three times with 150 µL/well of TBST (10 mM Tris-HCl pH 8.0, 150 mM NaCl, 0.05% Tween 20). To each well, 10 µL of 10% DMSO/TBST or compound (0.0001–100 µM) in 10% DMSO/TBST was incubated for 20 minutes at room temperature with 50 µL of 2.36 µM *E. coli* ProRS in TBST (10 mM Tris-HCL pH 8.0, 150 mM NaCl, 0.05% Tween 20). Following the preincubation, 40 µL of 0.391 µM Pro3-F in TBST was added to each well, mixed and incubated at room temperature for 60 minutes. The plate was then read in an LJL Analyst (LJL Biosystems, Sunnyvale, Calif.) in fluorescent polarization mode.

Figure 7:
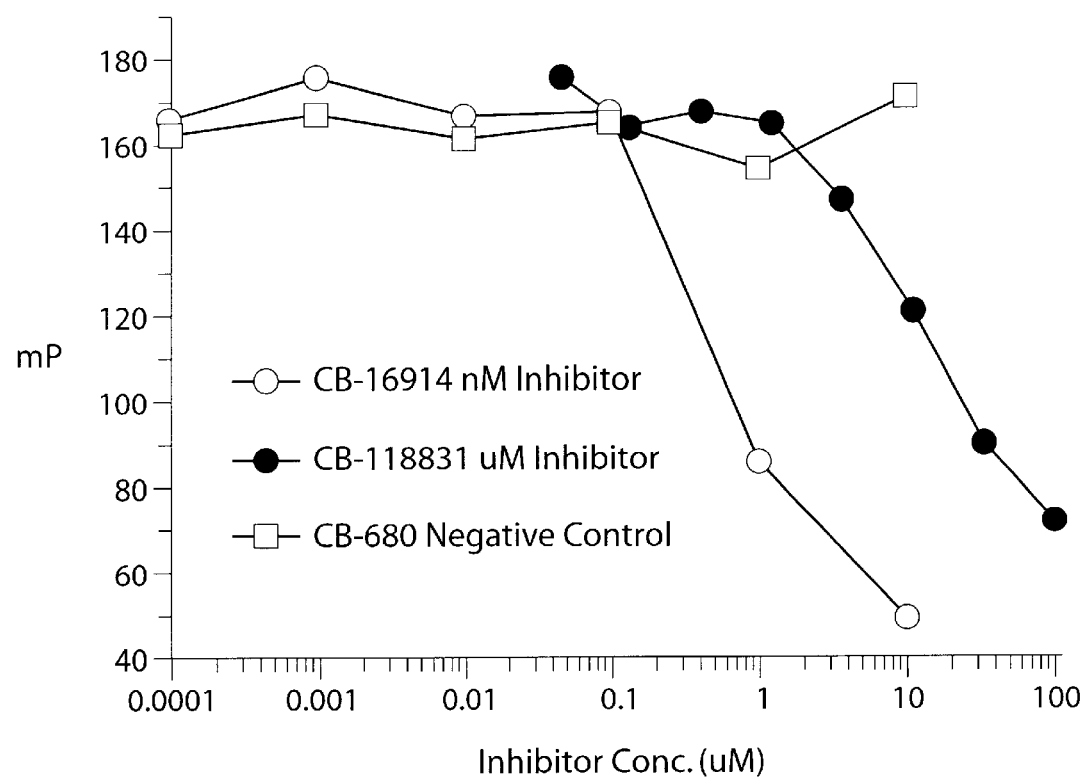
FIG. 7 is a graph showing fluorescence polarization plotted with the concentration of compound added, indicating inhibition of Pro3 peptide binding to *E. coli* ProRS in this assay by known inhibitors: open circles, CB-16914; filled circles, CB-118831; open squares, CB-680 negative control.

To assess the ability of the *E. coli* ProRS/Pro3-F FP binding assay to detect µM and nM inhibitors, three compounds were tested. CB-16914 and CB-118831 are known inhibitors of *E. coli* ProRS (nM and uM inhibitors, respectively) and CB-680 was used as a negative control. As shown in FIG. 7. both CB-16914 and CB-118831 were shown to inhibit Pro3-F binding whereas CB-680 had no effect.

FIG. 7 shows fluorescence polarization binding assay inhibition curves for CB-16914 (0.0001–10 µM), CB-]18831 (0.046–100 µM) and CB-680 (0.0001–10 µM) with 1.18 µM *E. coli* ProRS and 0.625 µM Pro3-F.

Example 9

Development of Assay for *S. aureus* MetRS and Met1 Peptide

A non-radioactive, homogeneous, sensitive fluorescent polarization (FP) assay has been developed for *Staphylococcus aureus* MetRS (Sa MetRS) and Met1 peptide. FP is a ratiometric detection method which is capable of discriminating between free and bound states of fluorescently labeled tracer based on differences in the rotation rates of the two states. The Sa MetRS FP binding assay involves the incubation of fluorescently labeled Met1 peptide (Met1-F) with purified Sa MetRS. In the bound state, Met1-F is bound to Sa MetRS and an increase in polarization signal is detected using a FP detection system. In the free state, Met1-F is not bound to Sa MetRS and there is a decrease in polarization signal.

See Example 7 for cloning and purification of SaMetRS. Sa MetRS GST fusion protein was cleaved with thrombin prior to these studies. Fluorescently labeled Met1 peptide (Met1-F) was synthesized and purified by SynPep Corp, Dublin Calif. Its sequence is shown below NH$_2$-DPNTWQLRWPMHGGK(FITC)-CO-amide (SEQ ID NO: 17)

A 96-well plate (Costar cat# 3915) was blocked for 1 hour at room temperature with 150 μL/well 2 mg/ml bovine serum albumin (BSA) (FisherBiotech cat# BP1600-100) in 0.1 M NaHCO$_3$. The plate was then washed manually three times with 150 μL/well of TBS (10 mM Tris-HCl pH 8.0, 150 mM NaCl). To each well, 20 μL of 5% DMSO/TBS or compound (0.0001–100 μM) in 5% DMSO/TBS was incubated for 20 minutes at room temperature with 80 μL of 0.025 μM Sa MetRS and 0.00625 μM Met1-F in reaction buffer (87.5 mM HEPES pH 7.5, 25 mM MgCl$_2$, 25 mM KCl, 25 μg/ml BSA, 5 mM DTT). The plate was then read in an LJL Analyst (LJL Biosystems, Sunnyvale Calif.) in fluorescent polarization mode.

To assess the ability of the Sa MetRS/Met1-F FP binding assay to detect 1M and nM inhibitors, seven compounds were tested as well as the unlabeled Met-1 peptide. The seven compounds are known inhibitors (IC$_{50}$'s in nM to μM range) of Sa MetRS functional charging assay. As shown in Table 7, six of the seven inhibitors showed similar IC$_{50}$'s (within 3–4×) in the FP binding assay as compared to the functional assay. The FP assay was unable to detect CB-125552 which may be due to (1) poor compound solubility or (2) compound binding at a site on Sa MetRS different from the site bound by the Met-1 peptide.

TABLE 7

IC$_{50}$ values for known Sa MetRS inhibitors: Comparison between the functional charging assay and the fluoresence polarization binding assay

| Inhibitor ID | Solubility | Mechanism of Inhibition | | IC$_{50}$ (μM) | |
|---|---|---|---|---|---|
| | | Methionine | ATP | Charging Assay | FP Binding Assay |
| CB-088887 | >100 | ND | ND | 26 | 60% remaining activity @ 100 μM |
| CB-098944 | ND | Competitive | Competitive | 3.1 | 9 |
| CB-114208 | 33 | Competitive | Competitive | 0.3 | 0.7 |
| CB-125265 | ND | Mixed | Mixed | 0.6 | 2 |
| CB-125552 | 11 | ND | ND | 13.4 | >100 |
| CB-126854 | >100 | ND | ND | 4.1 | 5 |
| MET-1 | >100 | Competitive | Competitive | 0.2 | 0.7 |
| peptide CB-00231 | >100 | Slow tight binding inhibitor | | 0.04 | 0.16 |

N = Not Determined

Figure 8:
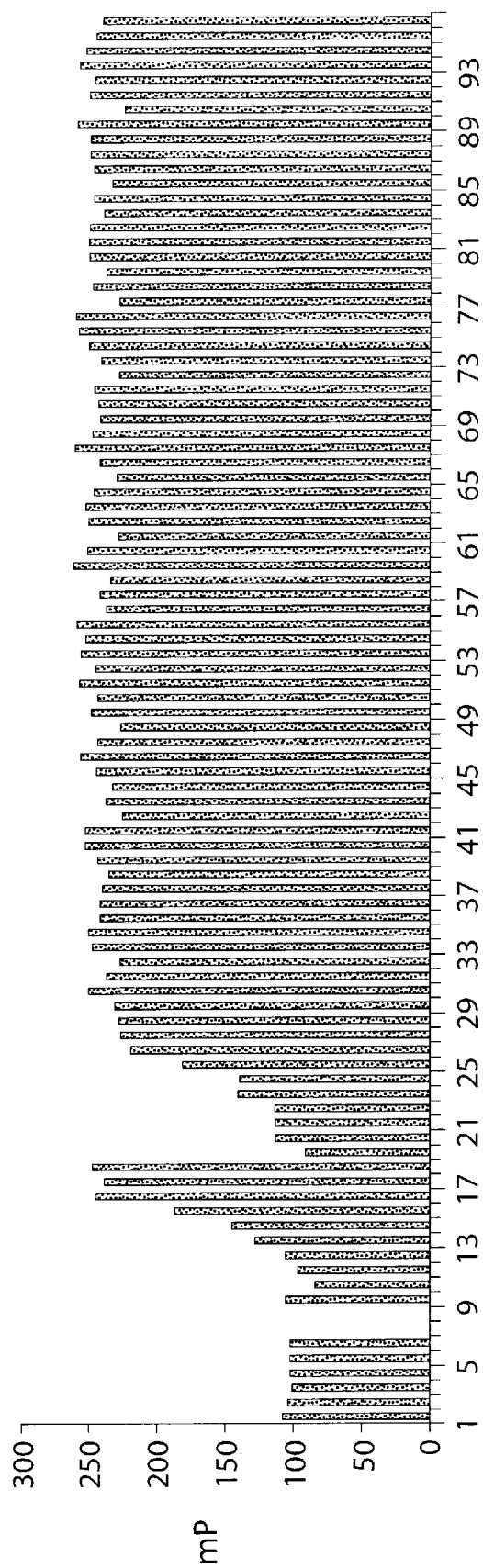
FIG. 8 is a bar graph showing fluorescence of microtiter wells in the assay described in Example 9. Wells 1–6 contain Met-1F alone. Wells 7 and 8 contain *S. aureus* MetRS (methionyl-tRNA synthetase) alone; wells 9–18 and 19–28 contain Met-1 peptide from 640 nM to 1.25 nM; wells 29–96 contain 1% DMSO (dimethyl sulfoxide).

The FP assay for Sa MetRS inhibition has been evaluated to see if it is amenable for high throughput screening (HTS) for drug discovery. The FP assay for Sa MetRS has been reduced to 96-well format and has been automated which is necessary for HTS. FIG. 8 shows results of an experiment on a control plate that was run to assess the performance of the FP HTS assay. Sa MetRS was at 20 nM final concentration; Met1-F was at 5 nM final concentration. Wells 1–6 contain Met-1F alone, wells 7–8 contain Sa MetRS alone, wells 9–18 and 19–28 contain Met1-F from 640 nM to 1.25 μM, wells 29–96 contain 1% DMSO. The mP range between free Met1-F and Met1-F bound by Sa MetRS was 141 mP. The IC$_{50}$ for Met1 was tested on the plate in duplicate and the results were consistent with previously determined values. The signal to noise for the plate assay (SIN) was 7:1 which is acceptable for HTS.

TABLE 8

| Plate Statistics | |
|---|---|
| mean mP | 244 |
| std dev | 9 |
| free peptide | 103 |
| mP range | 141 |
| CB-000231 | 245 ± 17 |
| IC$_{50}$ (μM) | |
| S/N | 7/1 |

All references cited herein are hereby incorporated by reference herein in their entirety.

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method for determining whether a biomolecule inhibits growth of cells in vivo, comprising:
   a) introducing a cell having an exogenous regulable gene encoding a biomolecule into one or more test animals and into one or more control animals, wherein the biomolecule binds a protein target component of the cells;
   b) regulating expression of the exogenous gene in the test animals to allow production of the biomolecule; and
   c) monitoring the test animals for growth of the cells wherein observing fewer of the cells or a slower growth rate of the cells in the test animals compared to the number of the cells or growth rate of the cells in the control animals indicates that the biomolecule inhibits growth of cells in vivo.

2. The method of clam 1, further comprising the step of first constructing the cell having the exogenous regulable gene encoding the biomolecule.

3. The method of claim 1, further comprising the steps of first
   i) constructing the cell having the exogenous regulable gene encoding the biomolecule;
   ii) regulating expression of the exogenous regulable gene in a culture of constructed cells, thereby producing the biomolecule in the constructed cells; and
   iii) monitoring growth of the constructed cells in culture, relative to growth of control cells, whereby, if growth is decreased in the constructed cell, compared to growth of the control cell, then the biomolecule inhibits growth in culture.

4. The method of claim 1, wherein the protein target component comprises a complex comprising more than one gene product.

5. The method of claim 1, wherein the protein target component consists of a single gene product.

6. The method of claim 1, wherein the protein target component comprises an enzyme.

7. The method of claim 1, wherein the biomolecule is a polypeptide or a peptide.

8. The method of claim 1, wherein the biomolecule is a fusion protein.

9. The method of claim 1, wherein the cell is a mammalian cell.

10. The method of claim 1, wherein the cell is a pathogen cell.

11. The method of claim 2, wherein the protein target component consists of a single gene product, a complex comprising more than one gene product, or an enzyme.

12. The method of claim 11, wherein the protein target component comprises an enzyme.

13. The method of claim 12, wherein the biomolecule is a polypeptide.

14. The method of claim 12, wherein the biomolecule is a peptide.

15. The method of claim 12, wherein the biomolecule is a fusion protein.

16. The method of claim 11, wherein the cell is a mammalian cell.

17. The method of claim 11, wherein the cell is a pathogen cell.

18. A method for determining whether a biomolecule inhibits infection by a pathogen cell in vivo, comprising
   a) introducing a pathogen cell having an exogenous regulable gene encoding a biomolecule into one or more test animals and into one or more control animals, wherein the biomolecule binds a protein target component of the pathogen cell;
   b) regulating expression of the exogenous gene in the test animals to allow production of the biomolecule; and
   c) monitoring the test animals for signs of infection wherein observing fewer or less severe signs of infection in the test animal compared to signs of infection in the control animal indicates that the biomolecule inhibits infection by the pathogen in vivo.

19. The method of claim 18, further comprising the step of first constructing the pathogen cell having the exogenous regulable gene encoding the biomolecule.

20. The method of claim 18, further comprising the steps of first
   i) constructing the pathogen cell having the exogenous regulable gene encoding the biomolecule;
   ii) regulating expression of the exogenous regulable gene in a culture of constructed pathogen cells, thereby producing the biomolecule in the constructed pathogen cells; and
   iii) monitoring growth of the constructed pathogen cells in culture, relative to growth of control cells, whereby, if growth is decreased in the constructed pathogen cell, compared to growth of the control cell, then the biomolecule inhibits growth in culture.

21. The method of claim 18, wherein the protein target component comprises a complex comprising more than one gene product.

22. The method of claim 18, wherein the protein target component consists of a single gene product.

23. The method of claim 18, wherein the protein target component comprises an enzyme.

24. The method of claim 18, wherein the biomolecule is a peptide or a polypeptide.

25. The method of claim 18, wherein the biomolecule is a fusion protein.

26. The method of claim 19, where the protein target component consists of a single gene product, a complex comprising more than one gene product, or an enzyme.

27. The method of claim 26, wherein the protein target component comprises an enzyme.

28. The method of claim 27, wherein the biomolecule is a polypeptide.

29. The method of claim 27, wherein the biomolecule is a peptide.

30. The method of claim 27, wherein the biomolecule is a fusion protein.

31. A method for identifying a compound which is a candidate for producing a phenotypic effect in a cell in vivo, said method comprising the steps of:

a) introducing a cell having an exogenous regulable gene encoding a biomolecule into one or more animals;

b) regulating expression of the exogenous gene in the animals to allow production of the biomolecule;

c) monitoring said cell in the animal for the phenotypic effect; and d) identifying, if the biomolecule caused the phenotypic effect, one or more compounds that competitively bind to a target cell component to which the biomolecule binds, whereby if the compound competitively binds to the target cell component, then the compound is a candidate for producing the phenotypic effect in vivo.

32. The method of claim 31, further comprising the step of first constructing the cell having the exogenous regulable gene encoding the biomolecule.

33. The method of claim 31, further comprising the steps of first i) constructing the cell having the exogenous regulable gene encoding the biomolecule;

ii) regulating expression of the exogenous regulable gene in a culture of constructed cells, thereby producing the biomolecule in the constructed cells; and ii.) monitoring growth of the constructed cells in culture, relative to growth of control cells, whereby, if growth is decreased in the constricted cell, compared to growth of the control cell, then the biomolecule inhibits growth in culture.

34. The method of claim 31, wherein the biomolecule is a polypeptide or a peptide.

35. The method of claim of claim 31, wherein the biomolecule is a fusion protein.

36. The method of claim 31, wherein the cell is a mammalian cell.

37. The method of claim 31, wherein the cell is a pathogen cell.

38. The method of claim 31 wherein the phenotypic effect is growth inhibition.

39. The method of claim 32 wherein the phenotypic effect is growth inhibition.

40. The method of claim 39 wherein the biomolecule is a peptide or polypeptide.

41. The method of claim 40, wherein the biomolecule is a fusion protein.

42. The method of claim 41 wherein the cell is a mammalian cell.

43. The method of claim 41 wherein the cell is a pathogen cell.

* * * * *

SEQUENCE LISTING

<160> NUMBER OF SEQ ID NOS: 18

<210> SEQ ID NO 1
<211> LENGTH: 15
<212> TYPE: PRT
<213> ORGANISM: Artificial Sequence
<220> FEATURE:
<223> OTHER INFORMATION: Synthetic

<400> SEQUENCE: 1

Ser Arg Asp Trp Gly Phe Trp Asp Trp Gly Val Asp Arg Ser
1               5                   10
Arg
 15

<210> SEQ ID NO 2
<211> LENGTH: 16
<212> TYPE: PRT
<213> ORGANISM: Artificial Sequence
<220> FEATURE:
<223> OTHER INFORMATION: Synthetic

<400> SEQUENCE: 2

Ser Arg Asp Trp Gly Phe Trp Arg Leu Pro Glu Ser Met Ala Ser Arg
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ser Arg Glu Trp His Phe Trp Arg Asp Tyr Asn Pro Thr Ser Arg
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Ser Ser Glu Arg Gly Ser Gly Asp Arg Gly Glu Lys Gly Ser Arg
1               5                   10                  15

<210> SEQ ID NO 5
<211> LENGTH: 43
<212> TYPE: DNA
<213> ORGANISM: Artificial Sequence
<220> FEATURE:
<223> OTHER INFORMATION: PCR Primer

<400> SEQUENCE: 5
ccaacaacat atgtcccgtg aatggcactt ctggcgtgac tac                          43

<210> SEQ ID NO 6
<211> LENGTH: 57
<212> TYPE: DNA
<213> ORGANISM: Artificial Sequence
<220> FEATURE:
<223> OTHER INFORMATION: PCR Primer

<400> SEQUENCE: 6
ttctggcgtg actacaaccc gacctcccgt gggggtggag gcatgtcccc tatacta        57

<210> SEQ ID NO 7
<211> LENGTH: 32
<212> TYPE: DNA
<213> ORGANISM: Artificial Sequence
<220> FEATURE:
<223> OTHER INFORMATION: PCR Primer

<400> SEQUENCE: 7
agttgaattc ttaatccgat tttggaggat gg        32

<210> SEQ ID NO 8
<211> LENGTH: 28
<212> TYPE: DNA
<213> ORGANISM: Artificial Sequence
<220> FEATURE:
<223> OTHER INFORMATION: PCR Primer

<400> SEQUENCE: 8
caaggtaccc atgtcccgtg aatggcac        28

<210> SEQ ID NO 9
<211> LENGTH: 31
<212> TYPE: DNA
<213> ORGANISM: Artificial Sequence
<220> FEATURE:
<223> OTHER INFORMATION: PCR Primer

<400> SEQUENCE: 9
cgcggatcct taatccgatt ttggaggatg g        31

<210> SEQ ID NO 10
<211> LENGTH: 31
<212> TYPE: DNA
<213> ORGANISM: Artificial Sequence
<220> FEATURE:
<223> OTHER INFORMATION: PCR Primer

<400> SEQUENCE: 10
aatccgctcg aggattattg ctattggtgc c        31

<210> SEQ ID NO 11
<211> LENGTH: 33
<212> TYPE: DNA
<213> ORGANISM: Artificial Sequence
<220> FEATURE:
<223> OTHER INFORMATION: PCR Primer

<400> SEQUENCE: 11
aatcgtaagc ttttattta agttatcata ttt        33

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Asp Pro Asn Thr Trp Gln Leu Arg Trp Pro Met His
 1               5                  10

<210> SEQ ID NO 13

```
<211> LENGTH: 12
<212> TYPE: PRT
<213> ORGANISM: Artificial Sequence
<220> FEATURE:
<223> OTHER INFORMATION: Synthetic

<400> SEQUENCE: 13

Met Trp Asp Leu Pro Tyr Ile Trp Ser Arg Pro Val
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic

<400> SEQUENCE: 14

Ala Asp Thr Leu Asn Trp Tyr Tyr Tyr Ala Ser Trp
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic

<400> SEQUENCE: 15

Ala Asn Asn Leu Ser Thr Met Lys Lys Leu Lys Gln
1               5                   10

<210> SEQ ID NO 16
<211> LENGTH: 22
<212> TYPE: PRT
<213> ORGANISM: Artificial Sequence
<220> FEATURE:
<223> OTHER INFORMATION: Synthetic

<400> SEQUENCE: 16

Ser Arg Glu Trp His Phe Trp Arg Asp Tyr Asn Pro Thr Ser Arg Gly
1               5                   10                  15

Gly Lys Phe Ile Thr Cys
            20

<210> SEQ ID NO 17
<211> LENGTH: 19
<212> TYPE: PRT
<213> ORGANISM: Artificial Sequence
<220> FEATURE:
<223> OTHER INFORMATION: Synthetic

<400> SEQUENCE: 17

Asp Pro Asn Thr Trp Gln Leu Arg Trp Pro Met His Gly Gly Lys Phe
1               5                   10                  15

Ile Thr Cys

<210> SEQ ID NO 18
<211> LENGTH: 4
<212> TYPE: PRT
<213> ORGANISM: Artificial Sequence
```

```
-continued

<220> FEATURE:
<223> OTHER INFORMATION: linker peptide

<400> SEQUENCE: 18

Glu Gly Gly Gly
 1
```